United States Patent [19]
Maier et al.

[11] Patent Number: 5,674,467
[45] Date of Patent: Oct. 7, 1997

[54] MESO-TETRAPHENYLPORPHYRIN COMPLEX COMPOUNDS, PROCESS FOR THEIR PRODUCTION AND PHARMACEUTICAL AGENTS CONTAINING THE LATTER

[75] Inventors: Franz Karl Maier; Wolfgang Ebert; Mary Lee-Vaupel; Heinz Gries; Jürgen Conrad, all of Berlin, Germany

[73] Assignee: Institut für Diagnostikforschung GmbH, Berlin, Germany

[21] Appl. No.: 513,935

[22] PCT Filed: Feb. 11, 1994

[86] PCT No.: PCT/DE94/00159

§ 371 Date: Sep. 26, 1995

§ 102(e) Date: Sep. 26, 1995

[87] PCT Pub. No.: WO94/19352

PCT Pub. Date: Sep. 1, 1994

[30] Foreign Application Priority Data

Feb. 17, 1993 [DE] Germany ............... 43 05 523.0

[51] Int. Cl.$^6$ .............. A61K 51/04; A61B 5/055; C07B 47/00; C07F 5/00
[52] U.S. Cl. ............... 424/1.65; 424/9.362; 540/145; 534/10; 534/15; 534/16; 514/185
[58] Field of Search ............... 424/1.65, 9.362; 540/145; 534/10, 15, 16; 514/185

[56] References Cited

U.S. PATENT DOCUMENTS 5,262,532 11/1993 Tweedle et al. ............... 540/145
5,284,647 2/1994 Niedballa et al. ............... 424/9.362

FOREIGN PATENT DOCUMENTS 0 336 879 10/1989 European Pat. Off. .

OTHER PUBLICATIONS

Keinan et al., "Catalytic Antibodies, Circular Dichroism and UV–Vis Studies of Antibody-Metalloporphyrin Interactions", Inorg. Chem., 31, 5433–5438, (1992).

Primary Examiner—Gary E. Hollinden
Assistant Examiner—Michael G. Hartley
Attorney, Agent, or Firm—Millen, White, Zelano, & Branigan, P.C.

[57] ABSTRACT

Porphyrin complex compounds consisting of a meso-tetraphenylporphyrin ligand of general formula I

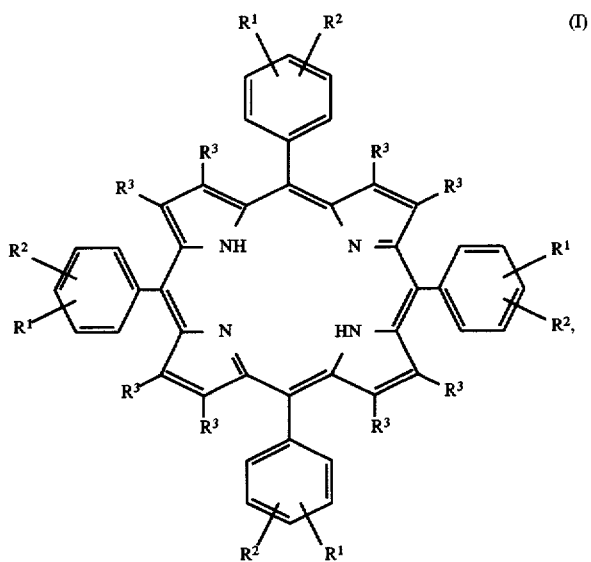

in which $R^1$, $R^2$ and $R^3$ have varying meanings, and an ion of an element of atomic numbers 21–32, 38, 39, 42–51 or 58–83 as well as optionally one or more physiologically harmless cation(s) of inorganic and/or organic bases, amino acids or amino acid amides are valuable diagnostic agents.

26 Claims, No Drawings

MESO-TETRAPHENYLPORPHYRIN COMPLEX COMPOUNDS, PROCESS FOR THEIR PRODUCTION AND PHARMACEUTICAL AGENTS CONTAINING THE LATTER

The invention relates to new meso-tetraphenylporphyrin complex compounds, new pharmaceutical agents containing these compounds, their use in diagnosis and therapy as well as process for the production of these compounds and agents.

The use of complexing agents or complexes or their salts has long been known in medicine. As examples, there can be mentioned: complexing agents are known as stabilizers of pharmaceutical preparations; complexes and their salts are known as additives for the administration of poorly soluble ions (e.g., iron); complexing agents and complexes (preferably calcium or zinc) optionally as salts with inorganic and/or organic bases, are known as antidote for detoxification in the case of inadvertent incorporation of heavy metals or their radioactive isotopes; and complexing agents are known as additives in nuclear medicine with use of radioactive isotopes such as $^{99m}Tc$ for scintiscanning. In Patents EP 71564, EP 130934 and DE-OS 3401052, complexes and complex salts have been presented as diagnostic agents, mainly as NMR diagnostic agents. These complexes and complex salts are quite well-tolerated and assure a separation of the ions that is complete to the greatest extent possible. Their parameters determining the effectiveness of an NMR contrast medium are not yet optimized, of which there are mentioned:

an advantageous relaxivity, so that the contrast medium in the smallest possible concentration reduces in vivo the relaxation time of the protons in the tissue water and other nuclei, such as P, F and Na, and thus makes possible, for example, the locating of tumors by increasing the signal intensity of the image obtained with the help of the nuclear spin tomograph; as selective as possible a concentration and/or retention of the contrast medium in the target organ; sufficient water solubility; low toxicity; good compatibility; good chemical and biochemical stability.

The complexes and complex salts of the mentioned patents are affected by the drawback that they are dispersed only relatively unspecifically in the extracellular space and therefore do not always make possible an identification of pathologically altered tissue. There is therefore a need particularly for selectively-bonding, tumor-specific compounds.

Relative to their compatibility, they should exhibit as great a safety margin as possible. As a measurement for it, the product from toxicity and relaxivity can be considered.

It has been known for several years now that porphyrin derivatives can accumulate selectively in human and animal tumors (D. Kessel and T. H. Chou, Cancer Res. 43, pp. 1994–1999, 1983, P. Hambright, Bioinorg. Chem. 5, pp. 87–92, 1975; R. Lipson et al., Cancer 20, pp. 2250–2257, 1967; D. Sanderson et al., Cancer 30, pp. 1368–1372, 1972). First attempts to use this family of compounds also as diagnostic agents have also been described (J. Winkelmann et al., Cancer Research 27, pp. 2060–2064, 1967; European Patent Application Publication No. 133603; N. J. Patronas et al., Cancer Treatment Reports 70, pp. 391–395, (1986).

The previously described compounds, however, are far from meeting the above-mentioned criteria in a satisfactory manner; their deficient concentration in the target organs increasingly calls for special attention. An improvement of this property should simultaneously help to reduce the existing problems with the toxicity and compatibility of the previously known compounds.

In Patent Application EP 0336879, substituted meso-tetraphenylporphyrin complex compounds for use in diagnosis and therapy are described. These compounds show a good concentration behavior in various target organs, but the described compounds in use as NMR diagnostic agents exhibit a ratio between the dose necessary for optimum imaging and the lethal dose that is not yet completely satisfactory.

Therefore, for varied purposes, there is further a need for stable, readily soluble but also better compatible and selectively-bonding complex compounds, which are suitable for the diagnosis and/or also treatment, for example, of tumors.

The object of the invention is to make available these compounds and pharmaceutical agents as well as to provide a process for their production.

This object is achieved by the invention.

It has been found that the porphyrin complex compounds according to the invention, consisting of new meso-tetraphenylporphyrin ligands and ions of an element of atomic numbers 21–32, 38, 39, 42–51 or 57–83 as well as optionally one or more cation(s) of inorganic and/or organic bases, amino acids or amino acid amides, are surprisingly very well suited for the production of NMR diagnostic agents, radiodiagnostic agents and radiotherapeutic agents.

The porphyrin complex compounds according to the invention consist of a meso-tetraphenylporphyrin ligand of general formula I

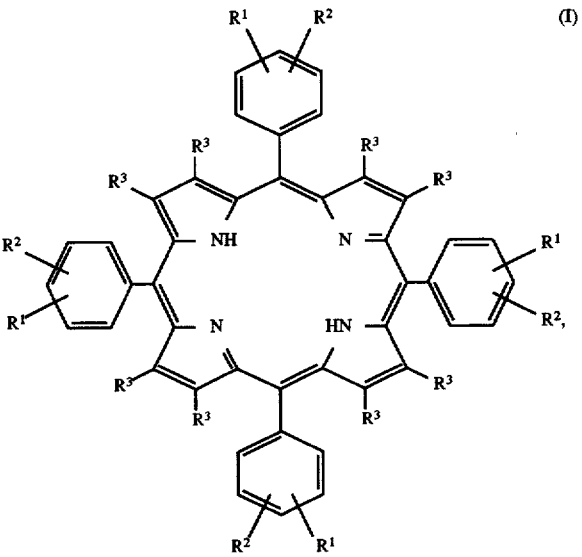

in which $R^1$ stands for a V—CO—A, V—SO$_2$—A, V—PO (A)$_2$ or N(E)—CH$_2$—C(=O)—A radical with A meaning an OH, OR$^4$ or NR$^5$R$^6$ group, in which R$^4$ means a C$_1$–C$_6$ alkyl or benzyl radical, R$^5$ and R$^6$, independently of one another, mean hydrogen, a straight-chain or branched-chain or cyclic, saturated or unsaturated, aliphatic hydrocarbon radical with up to 16 atoms, optionally substituted by one or more hydroxy or lower alkoxy groups, or R$^5$, if R$^6$ is a hydrogen atom, means an aryl or aralkyl group optionally substituted by one or more di—C$_1$–C$_6$ alkylamino groups or by a C$_1$–C$_6$ alkoxy group, or $R^5$ and $R^6$ together with the nitrogen atom mean a saturated or unsaturated 5- or 6-ring, optionally containing another nitrogen, oxygen, sulfur atom or a carbonyl group, which optionally is substituted by one or more $C_1$–$C_6$ alkyl, $C_1$–$C_5$ hydroxyalkyl radical(s), an optionally hydroxylated or $C_1$–$C_6$ alkoxylated $C_2$–$C_6$ acyl, hydroxy, carbamoyl, carbamoyl-substituted $C_1$–$C_6$ alkyl radical(s), carbamoyl radical or (a) $C_1$–$C_6$ acylamino or $C_1$–$C_6$ alkylamino radical(s) substituted on the carbamoyl-nitrogen by one or two $C_1$–$C_6$ alkyl radical(s)—which also can form a ring optionally containing an oxygen atom, V meaning a straight-chain, branched, saturated or unsaturated $C_1$–$C_{20}$ alkylene group optionally containing imino, $NR^7$, polyethylenoxy, phenylene, phenylenoxy, phenylenimino, amido, sulfonamido, hydrazido, ester group(s), oxygen, sulfur and/or nitrogen atom(s), optionally substituted by hydroxy, mercapto, imino, epoxy, oxo, thioxo and/or amino group(s), as well as—if $R^1$ means a V—PO—$(A)_2$ radical—a direct bond, in which $R^7$ means a $C_1$–$C_{10}$ alkyl group, a benzenesulfonyl group or a $C_1$–$C_4$ alkylphenylenesulfonyl group optionally containing a carbonyl, phenylene, sulfonyl group, optionally substituted by a carboxyl group, E meaning a $C_1$–$C_4$ acyl, $C_1$–$C_{10}$ alkylsulfonyl, benzenesulfonyl, $C_1$–$C_4$ alkylphenylenesulfonyl, carboxy-$C_1$–$C_6$ alkyl or carboxy-$C_1$–$C_5$ acyl group.

$R^2$ stands for one of the substituents indicated for $R^1$ or $R^3$ and $R^3$ stands for a hydrogen, fluorine, chlorine, iodine atom or a straight-chain or branched $C_1$–$C_4$ alkyl radical, and an ion of an element of atomic numbers 21–32, 38, 39, 42–51 or 57–83 as well as optionally one or more physiologically harmless cation(s) of inorganic and/or organic bases, amino acids or amino acid amides.

In particular, porphyrin complex compounds can be mentioned, which are characterized in that they consist of a meso-tetraphenylporphyrin ligand of general formula II

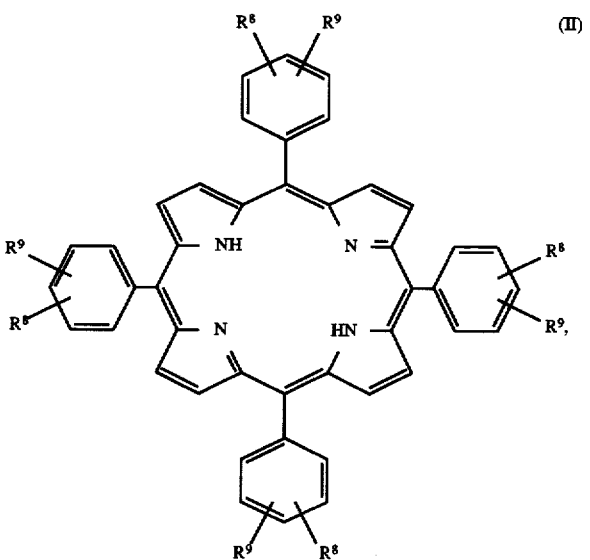

in which $R^8$ stands for a radical —$(O)_s$—$(CH_2)_k$—X—$CH_2$—Y—C(=O)—Z with s meaning numbers 0 or 1, k meaning numbers 0, 1, 2 or 3, X meaning an oxygen atom, a direct bond or an —$NR^{10}$ group, in which $R^{10}$ stands for a $C_1$–$C_4$ acyl, $C_1$–$C_{10}$ alkylsulfonyl, benzenesulfonyl, $C_1$–$C_4$ alkylphenylene-sulfonyl, carboxy-$C_1$–$C_6$ alkyl or carboxy-$C_1$–$C_5$ acyl group, Y meaning a direct bond or a —CHOH group and Z meaning an —OH or —N $(R^{11})$—$R^{12}$ group, in which $R^{11}$ and $R^{12}$, independently of one another, stand for hydrogen or for a straight-chain or branched-chain or cyclic, saturated or unsaturated hydrocarbon radical with up to 16 C atoms, optionally substituted by 1–6 hydroxy groups, provided that no direct O—O or O—N bonds are to be permitted, $R^9$ stands for a hydrogen, fluorine, chlorine, bromine, iodine atom, a straight-chain or branched $C_1$–$C_4$ alkyl radical or for one of the substituents indicated for $R^8$, and an ion of an element of atomic numbers 21–32, 38, 39, 42–51 or 58–83 as well as optionally one or more physiologically harmless cation(s) of inorganic and/or organic bases, amino acids or amino acid amides.

If the agents according to the invention are intended for use in NMR diagnosis, paramagnetic metal ions must be present in the complex. These are especially the divalent and trivalent ions of the elements of atomic numbers 21–29, 42, 44 and 58–70. Suitable ions are, for example, the chromium (III), manganese(III), iron(III), cobalt(II), cobalt(III), nickel (II), copper(II), praseodymium(III), neodymium(III), samarium(III), gadolinium(III), terbium(III), dysprosium (III), holmium(III), erbium(III) and ytterbium(III) ions. Especially preferred is the manganese(III) ion because of the high stability and the high magnetic moment of its porphyrin complex. For radiodiagnosis and radiotherapy, complexes that contain a radioisotope of elements 27, 29–32, 38, 39, 42–51, 62, 64, 70, 75, 77, 81, 82 or 83 as central atom are suitable. Especially suitable are, for example, radioisotopes of the elements copper, cobalt, gallium, germanium, yttrium, strontium, technetium, indium, ytterbium, gadolinium, samarium, thallium and iridium.

If one of the ions complexed by a porphyrin ligand is present in a higher oxidation stage than +2, the excess charge(s) is (are) balanced by anions of organic or inorganic acids, preferably by acetate and chloride anions, optionally also by oxide and nitride anions.

The complexes according to the invention surprisingly show a clearly higher relaxivity relative to previously known, structurally similar compounds. Since the relaxivity provides a reference to the effectiveness of the contrast medium of a compound, a comparable, positive signal effect is possible even in a lower dose with the use of the complexes according to the invention in the area of NMR diagnosis. As a result, the safety margin increases significantly, for which the product, from relaxivity and compatibility, can be considered as a guide value.

In direct comparison also to the compounds described in Patent Application EP 0 336 879, the compounds according to the invention have turned out to be superior relative to their effectiveness and their compatibility (see Table, Example 17). With the help of the complex compounds according to the invention, surprisingly not only tumor tissue and individual organs, such as, for example, liver, kidney and lymph nodes, but also blood vessels can be visualized in vivo without using special pulse-sequences, with which they can be used as perfusion agents, i.a.

As alkyl substituents $R^4$, hydrocarbons with 1–6, preferably 1–4 C atoms, such as, for example, methyl, ethyl, propyl, isopropyl, n-, sec- or tert-butyl, isobutyl, pentyl and hexyl radicals, are considered.

As alkyl substituents $R^5$ and $R^6$, or $R^{11}$ and $R^{12}$, saturated, unsaturated, straight-chain or branched-chain or cyclic hydrocarbons with up to 16 C atoms, preferably saturated hydrocarbons with 1 to 10 C atoms, especially saturated hydrocarbon atoms with 1 to 7 C atoms, are considered, which optionally are substituted by 1 to 5 hydroxy groups or, in the case of $R^5$ and $R^6$, by 1 to 5 lower alkoxy groups.

Lower alkoxy groups are to contain 1 to 4 carbon atoms in each case and in particular comprise methoxy and ethoxy groups.

As optionally substituted alkyl groups, there can be mentioned, for example, the methyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl and 2-methoxyethyl groups.

If $R^6$ stands for a hydrogen atom, $R^5$ can also mean a $C_6$–$C_{10}$ aryl or $C_6$–$C_{10}$—Ar—$C_1$–$C_6$ alkyl group, for example, phenyl or benzyl group, optionally substituted by one or more (up to three) di—$C_1$ to $C_6$ alkylamino groups or by one or more (up to three) $C_1$ to $C_6$ alkoxy groups.

The heterocyclic 5- or 6-ring formed by $R^5$ and $R^6$ under the action of amide nitrogen can be saturated, unsaturated and/or substituted, and optionally can contain a nitrogen, oxygen, sulfur atom or a carbonyl group.

The heterocycle can be substituted by a hydroxy group, a $C_1$–$C_6$ alkyl group, for example, methyl, ethyl, propyl, isopropyl, butyl group, a $C_1$–$C_5$ hydroxyalkyl group, for example, hydroxymethyl, hydroxyethyl, or by a $C_2$–$C_6$ acyl group, for example, acetyl, propionyl, which optionally can be substituted by a hydroxy or $C_1$–$C_6$ alkoxy group, for example, methoxy, ethoxy.

As another substituent, the carbamoyl group can be mentioned, which is bound directly or by a $C_1$–$C_6$ alkylene group, for example, methylene, ethylene, propylene, separately on the heterocycle and optionally is substituted on nitrogen by one or two $C_1$–$C_6$ alkyl radical(s), for example, methyl, ethyl, propyl, isopropyl, which optionally form a ring, such as, for example, a pyrrolidine or piperidine ring. The carbamoyl nitrogen can also be a component of a morpholine ring.

As another possible substituent on the heterocycle, a $C_1$–$C_6$ alkylated or a $C_1$–$C_6$ acylated primary or secondary amino group, such as, for example, the methyl, ethyl, acetyl, propionyl-amino group, can be mentioned.

If the heterocycle is substituted, the total number of substituents is 1 to 3. As suitable heterocycles, there can be mentioned as examples: the pyrrolidinyl, piperidyl, pyrazolidinyl, pyrrolinyl, pyrazolinyl, piperazinyl, morpholinyl, imidazolidinyl, oxazolidinyl, thiazolidinyl rings.

For $R^7$ and $R^{10}$ or E, there can be mentioned, for example: the formyl, acetyl, propionyl, n-butyryl, i-butyryl, methanesulfonyl, ethanesulfonyl, propanesulfonyl, butanesulfonyl, pentanesulfonyl, hexanesulfonyl, heptanesulfonyl, octanesulfonyl, nonanesulfonyl, decanesulfonyl, benzenesulfonyl, p-toluenesulfonyl, 4-ethyl-phenylsulfonyl, carboxyhexyl, carboxypentyl, carboxybutyl, carboxypropyl, carboxyethyl, carboxymethyl, 5-carboxyvaleroyl, 4-carboxybutyryl, 3-carboxypropionyl, carboxyacetyl, carboxycarbonyl radicals.

The alkylene group standing for V can be straight-chain, branched, cyclic, aliphatic, aromatic or arylaliphatic, exhibit up to 20 carbon atoms and optionally contain —NH—, —O—, —S—, —N—, —CO—O—, —O—CO—, (O—CH$_2$CH$_2$)poly, —NH—CO—, —CO—NH—, —N(SO$_2$—)—, —N(CO—)—, —N(CH$_2$—)—, —NH—NH—; —C$_6$H$_4$—NH—, —C$_6$H$_4$—O—, —C$_6$H$_4$— groups. Preferred are the straight-chain $C_1$–$C_6$ methylene groups.

For clarification, the following alkylene groups can be mentioned as examples:
—(CH$_2$)$_2$NH—; —CH$_2$—O—C$_6$H$_4$—CH$_2$—; CH$_2$—CH(OH)—CH$_2$—O—C$_6$H$_4$—CH$_2$—; —C(=NH)—O—C$_6$H$_4$—CH$_2$—; (CH$_2$)$_4$—NH—CO—CH$_2$—O—C$_6$H$_4$—CH$_2$—; —(CH$_2$)$_4$—NH—CH$_2$—CH(OH)—CH$_2$—O—C$_6$H$_4$—CH$_2$—; —(CH$_2$)$_3$—O—C$_6$H$_4$—CH$_2$—; —CH$_2$—CO—NH—(CH$_2$)$_3$—O—CH$_2$—; —CH$_2$—CO—NH—NH—; —CH$_2$—CO—NH—(CH$_2$)$_2$; —CH$_2$—CO—NH—(CH$_2$)$_{10}$—; —CH$_2$—CO—NH—(CH$_2$)$_2$—S—; —(CH$_2$)$_4$—NH—CO—(CH$_2$)$_8$—; —CH$_2$—CO—NH—(CH$_2$)$_3$—NH—; —(CH$_2$)$_3$—NH—; —(CH$_2$)—NH—C(=S)—NH—C$_6$H$_4$—CH$_2$—; —(CH$_2$)$_2$—NH—CO—CH$_2$—(OCH$_2$CH$_2$)$_{43}$—OCH$_2$—, —O—(CH$_2$)$_3$N(CO—CH$_3$)—CH$_2$—, CH$_2$—N(SO$_2$—C$_6$H$_4$—CH$_3$)—CH$_2$—.

Especially preferred are:
—CH$_2$—, —CH$_2$—CH$_2$—, —O—CH$_2$—, —N(CO—CH$_3$)CH$_2$—, —N(CH$_3$)—CH$_2$—, —N(CH$_2$—COOH)CH$_2$—, —O—CH$_2$—(CHOH)—, O—(CH$_2$)$_3$—N(CO—CH$_3$)—CH$_2$—, —CH$_2$—N(SO$_2$—C$_6$H$_4$—CH$_3$)—CH$_2$—, O—CH$_2$)$_3$—N(SO$_2$—C$_6$H$_4$—CH$_3$)—CH$_2$—.

In $R^1$ and/or $R^2$ or $R^8$ and/or $R^9$, optionally present acid hydrogen atoms can optionally be replaced completely or partially by cations of inorganic and/or organic bases or amino acids or amino acid amides.

Suitable inorganic cations are, for example, the lithium ion, the potassium ion, the calcium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, of arginine and of ornithine as well as the amides of otherwise acidic or neutral amino acids.

The production of the porphyrin complex compounds of formula I according to the invention takes place in that porphyrins of general formula III

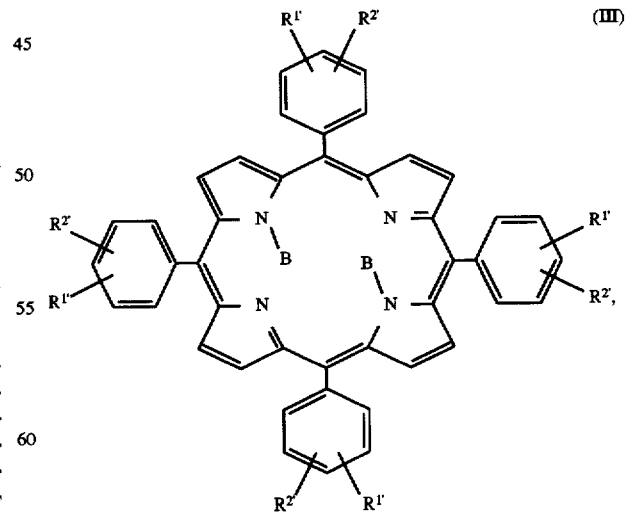

in which
B stands for a hydrogen atom or a metal ion equivalent of an element of atomic numbers 21–32, 38, 39, 42–51 and 58–83, R¹' stands for a radical V'—CO—A', —V'—SO₂—A', —V'—PO(A')₂ or N(E')—CH₂—C(=O)—A' radical with V' and E' in the meaning indicated for V and E, in which functional groups optionally contained in V and E, however, optionally are protected, and A' meaning a leaving group or—in which B must stand for a hydrogen atom—for the OR⁴ group.

R²' stands for one of the substituents indicated for R¹' or R³' are saponified or reacted with an amine of general formula IV $$H N R^{5'} R^{6'},\qquad (IV)$$

in which

R⁵' and R⁶' have the meaning indicated for R⁵ and R⁶, in which hydroxy groups optionally contained in R⁵ and R⁶, however, are optionally protected, optionally present protective groups are cleaved, and in the cases where B stands for a hydrogen atom, reacted with a metal oxide or metal salt of an element of atomic numbers 21–32, 38, 39, 42–51 or 58–83—in which the sequence of the two last-mentioned reactions can be interchanged—and optionally then the acid hydrogen atoms that are optionally still present in the thus obtained porphyrin complex compounds are substituted by cations of inorganic and/or organic bases, amino acids or amino acid amides.

The production of the porphyrin complex compounds of formula II takes place in that porphyrins of general formula V

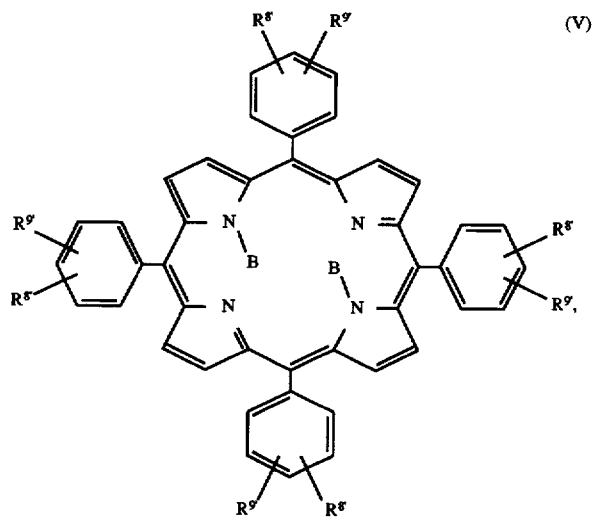

in which

B stands for a hydrogen atom or a metal ion equivalent of an element of atomic numbers 21–32, 38, 39, 42–51 or 58–83, R⁸' stands for a radical —(O)ₛ—(CH₂)ₖ—X'—CH₂—Y'—C(=O)—Z' with X' and Y' in the meaning indicated for X and Y, in which functional groups optionally contained in X and Y, however, are optionally protected and Z' meaning a leaving group, R⁹' stands for R⁹ or for one of the substituents indicated for R⁸', are saponified or reacted with an amine of general formula VI $$H N R^{11'} R^{12'},\qquad (VI)$$

in which

R¹¹' and R¹²' have the meaning indicated for R¹¹ and R¹², in which hydroxy groups optionally contained in R¹¹ and R¹², however, are optionally protected, optionally present protective groups are cleaved and in the cases where B stands for a hydrogen atom, reacted with a metal oxide or metal salt of an element of atomic numbers 21–32, 38, 39, 42–51 or 58–83—in which the sequence of the two last-mentioned reactions can be interchanged—and optionally then acid hydrogen atoms optionally still present in the thus obtained porphyrin complex compounds are substituted by cations of inorganic and/or organic bases, amino acids and amino acid amides.

Functional groups in precursors of the compounds according to the invention with increments and radicals X, Y, V, E, R⁵, R⁶, R¹¹, R¹² in the above-mentioned meaning can be provided with protective groups to assure, e.g., selective reactions, an easier purification or good solubility in organic solvents.

Thus, carboxy functions optionally contained in V, E and X are protected as esters. Preferred are methyl, ethyl, isopropyl and tert-butyl esters. Hydroxy groups, which can be contained in V, Y, R⁵, R⁶, R¹¹, R¹², can be protected, for example, as esters, diols or acetals. The acetyl radical as protective group is preferred especially for monovalent alcohols; furthermore, (the) isopropylidene and (the) benzylidene radical(s) is (are) especially preferred for the protection of diols and optionally also of higher-valent alcohols.

The introduction and cleavage of protective groups is possible in a way known in the art (Th. W. Greene, P. G. M. Wuts: Protective Groups in Organic Synthesis, John Wiley & Sons Inc. (1991) 10, 143, 224).

A' or Z' in the above-mentioned meaning as leaving groups can stand, e.g., for halide, alcoholate, acyloxy, alkyloxycarbonyloxy radicals.

If carboxy or carboxylate functions are to result by cleavage or conversion of radicals A' or Z', methoxy, ethoxy, propoxy or tert-butoxy radicals are preferred for A' or Z'. Relative to the blocking and release of the carboxy or carboxylate functions, reference can be made to the literature cited above for handling protective groups.

If radicals A' or Z' are to be used as a nucleofuge in the acylation of amines of general formulas IV or VI, the following radicals are preferred for A' or Z': the chlorine, bromine, iodine, methoxy, ethoxy, propoxy, acetoxy, methoxycarboxy, ethoxycarboxy, n-propoxycarboxy, i-propoxycarboxy, i-butoxycarboxy, tert-butoxycarboxy, 2-ethylhexyloxycarboxy, benzyloxycarboxy, 2,5-dioxopyrrolidin-1-yl-oxy, benzotriazol-1-yl-oxy and the trimethylsilyloxy radical.

The conditions for production of activated carbonyl compounds and their reaction to amides are known in the literature (R. C. Larock, Comprehensive Organic Transformations, VCH Verlagsgesellschaft [Publishing Company] mbH Weinheim (1989), p. 963, Houben-Weyl, Methoden der Organischen Chemie [Methods of Organic Chemistry], Georg Thieme-Verlag, Stuttgart, Volume E5 (1985), 633; Org. Reakt. 12, 157 (1952)). For the production of the desired amides, there can be mentioned as suitable amines of general formulas IV and VI, for example:

Dimethylamine, diethylamine, di-n-propylamine, diisopropylamine, di-n-butylamine, diisobutylamine, di-sec-butylamine, N-methylpropylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, morpholine, pyrrolidine, piperidine, N-methylpiperazine, N-ethylpiperazine, N-(2-hydroxyethyl)-piperazine, N-(hydroxymethyl)piperazine, piperazinoacetic acid isopropyl amide, N-piperazinomethylcarbonyl)-morpholine, N-(piperazinomethylcarbonyl)-pyrrolidine, 2-(2-hydroxymethyl)-piperidine, 4-(2-hydroxyethyl)-piperidine, 2-hydroxymethylpiperidine, 4-hydroxymethylpiperidine, 2-hydroxymethyl-pyrrolidine, 3-hydroxymethyl-piperidine, 4-hydroxypiperidine, 3-hydroxy-pyrrolidine, 4-piperidone, 3-pyrroline, piperidine-3-carboxylic acid amide, piperidine-4-carboxylic acid amide, piperidine-3-carboxylic acid diethylamide, piperidine-4-carboxylic acid dimethylamide, 2,6-dimethylpiperidine, 2,6-dimethylmorpholine, N-acetylpiperazine, N-(2-hydroxy-propionyl)-piperazine, N-(3-hydroxypropionyl)-piperazine, N-(methoxyacetyl)-piperazine, 4-(N-acetyl-N-methylamino)-piperidine, piperidine-4-carboxylic acid-(3-oxapentamethylene)-amide, piperidine-3-carboxylic acid-(3-oxapentamethylene)-amide, N-(N',N'-dimethylcarbamoyl)-piperazine, pyrazoline, imidazoline, oxazolidine, thiazolidine, 2,3-dihydroxypropylamine, N-methyl-2,3-dihydroxypropylamine, 2-hydroxy-1-(hydroxymethyl)-ethylamine, N,N-bis-(2-hydroxyethyl)-amine, N-methyl-2,3,4,5,6-pentahydroxyhexylamine, 6-amino-2,2-dimethyl-1,3-dioxepin-5-ol, 2-hydroxyethylamine, 2-amino-1,3-propanediol, diethanolamine, ethanolamine.

The polyhydroxyalkylamines can advantageously also be used in protected form for reaction, for example, as O-acyl derivatives or as ketals. This holds true especially if these derivatives can be produced more easily and more inexpensively than the polyhydroxyalkylamines themselves. A typical example is the 2-amino-1-(2,2-dimethyl-1,3-dioxolan-4-yl)-ethanol, the acetonide of 1-amino-2,3,4-trihydroxybutane, produced according to DE-OS 31 50 917.

The subsequent removal of the protective groups is problem-free and can take place, for example, by treatment with an acid ion exchanger in aqueous-ethanolic solution.

The introduction of the desired metals (e.g., Mn, Fe, Co, Ni, Cu, Zn, Tc, Sm, Eu, Gd, Tl, Bi) into porphyrins takes place according to methods known in the literature (The Porphyrins, ed. D. Dolphin, Academic Press, New York 1980, Vol. V, p. 459), and basically there can be mentioned:

a) the substitution of pyrrolic NH's (by heating the metal-free ligand with the corresponding metal salt, preferably acetate, optionally by the addition of acid-buffering agents, such as, e.g., sodium acetate, in a polar solvent) or b) the "recomplexing" in which a metal already complexed by ligands (e.g., zinc) is displaced by the desired metal (e.g., manganese).

As solvent, particularly polar solvents, such as, e.g., methanol, glacial acetic acid, pyridine, N,N-dimethylformamide, dichloromethane, chloroform and water, are suitable.

For the production of nuclear-medicine preparations with a short half-life of the central atom, it is generally advisable to incorporate the desired metal in the porphyrin ligand in the last step of the synthesis. Otherwise, it is advantageous in most cases to remove optionally present protective groups on the porphyrin ligand only after introduction of the desired metal by—as described above—methods usual in organic chemistry, since the protected compounds can be purified easily because of their solubility in organic solvents, e.g., by shaking out, recrystallization or chromatographic methods.

In most cases, the production of meso-tetraphenylporphyrins takes place in that an optionally appropriately substituted pyrrole is reacted with a suitable mono- or disubstituted benzaldehyde to the macrocycle by Rothemund reaction (P. Rothemund, J. Am. Chem. Soc. 57, 2010 (1935); 61, 2912 (1939))—or a variant of this method (A. D. Adler, F. R. Longo, J. D. Finarelli, J. Goldmacher, J. Assour and J. Korsakoff, J. Org. Chem. 32, 476 (1967); O. Bortolini, M. Ricci, B. Meunier, P. Friant, I. Ascone and J. Goulon, Nouv. J. Chimie [New J. Chemistry] 10, 39 (1986); C. L. Hill and M. M. Williamson, J. Chem. Soc., Chem. Commun. 1228 (1985); P. S. Traylot, D. Dolphin and T. G. Traylor, J. Chem. Soc. Chem. Commun. 279 (1984); J. S. Lindsey, I. C. Schreiman, H. C. Hsu, P. C. Kearney and A. M. Marguerettaz, J. Org. Chem. 52, 827 (1987); A. W. van der Made, E. J. H. Hoppenbrouwer, R. J. M. Nolte and W. Drenth, Recl. Trav. Chim. Pays-Bas [Recl. Tray. Chem. of The Netherlands] 107, 15–16 (1988)).

For this purpose, especially preferred pyrroles are pyrrole, 3,4-dimethylpyrrole and 3,4-diethylpyrrole (CA 109 (9): 73206a).

Preferred benzaldehyde derivatives are, e.g., 2-hydroxybenzaldehyde, 3-hydroxybenzaldehyde, 4-hydroxybenzaldehyde, 2,3-dihydroxybenzaldehyde, 3,4-dihydroxybenzaldehyde, which are commercially available. It is generally advantageous to provide the hydroxy function of the indicated benzaldehyde derivatives before the Rothemund reaction with suitable protective groups, e.g., with methyl, acetyl or benzyl protective groups, which can be easily removed again after the synthesis of the macrocycle. (Th. W. Greene, P. G. M. Wats: Protective Groups in Organic Synthesis, John Wiley R. Sons Inc., (1991) 10, 143; Michel Momenteau et al., J. Chem. Soc., Perkin Trans. 1 (1983) 189).

Especially preferred benzaldehyde derivatives are 3-bromomethylbenzaldehyde (B. C. Bookser and T. C. Brenice, J. Am. Chem. Soc. 1991, 113, 4208–4218), (2-formylphenoxy)-acetic acid-i-propyl ester (CA 84 (11): 74117z; 80 (15): 82705 z), 2,2'-[(4-formyl-1,2-phenylene)-bis(oxy)]-bis-acetic acid diethyl ester (CA 110 (13): 114844 y), (3-formylphenyl)-acetic acid methyl ester (Baker et al., J. Chem. Soc. 1956, 404, 413), 3-(3-formylphenyl)-propionic acid ethyl ester (CA 107 (3): 115500 h), N,N-bis-[(1-methylethyl)-oxycarbonylmethyl]-3-aminobenzaldehyde (see Example 8b).

While alkyl substituents on the pyrrole ring of porphyrin are generally advantageously established by using correspondingly substituted pyrrole for the Rothemund reaction (see above), halogen substituents are readily introduced by halogenation of porphyrin in its pyrrole rings (e.g., S. Onaka et al., Poster 34, 29th International Conference on Coordination Chemistry, Lausanne, Switzerland (1992)).

The following porphyrins are especially preferred as starting material or as intermediate stage for the production of porphyrin complex compounds according to the invention: 5,10,15,20-tetrakis-(2-hydroxyphenyl)-porphyrin, 5,10,15,20-tetrakis-(3-hydroxyphenyl)-porphyrin, 5,10,15,20-tetrakis-(4-hydroxyphenyl)-porphyrin (R. Bonnett et al., Photobiochemistry and Biophysics, Suppl. (1987) 45–56), 5,10,15,20-tetrakis-(3-acetylaminophenyl)-porphyrin (Example 5a), 5,10,15,20-tetrakis-(3-bromo-methylphenyl)-porphyrin, 5,10,15,20-tetrakis-(3-aminomethylphenyl)-porphyrin, 5,10,15,20-tetrakis-[3-(p-toluenesulfonamidomethyl)-phenyl]-porphyrin (T. C. Bruice et al., J. Am. Chem. Soc. 1991, 113, 4208), 5,10,15,20-tetrakis-(3-cyanomethylphenyl)-porphyrin (T. C. Bruice et al., J. Org. Chem. 56 (11), 3470 (1991)).

The etherification especially of phenolic OH groups in tetraphenylporphyrins is possible with electrophiles that are standard in organic chemistry, such as, e.g., appropriately substituted alkyl chlorides, alkyl bromides, alkyl iodides, alkyl tosylates or epoxides (Houben-Weyl, Methoden der organischen Chemie, Volume VI/3, Georg Thieme Verlag Stuttgart (1965), 7). As solvent, both nonpolar solvents, such as, e.g., toluene and benzene, especially with use of phasetransfer catalysts (e.g., triethylbenzylammonium bromide), polar aprotic solvents, e.g., diethyl ether, tetrahydrofuran, dioxane, N,N-dimethylformamide and dimethyl sulfoxide and protic solvents, such as, e.g., water, methanol, ethanol and as auxiliary bases, e.g., tertiary amines, such as triethylamine or inorganic bases, e.g., lithium, sodium or potassium carbonate; lithium, sodium or potassium hydrogen carbonate; lithium, sodium or potassium hydroxide, are used. Primary carboxylic acid or sulfonic acid amide functions in tetraphenylporphyrin substituents can be reacted with suitable alkylating agents in secondary carboxylic acid or sulfonic acid amides (Houben-Weyl, Methoden der organischen Chemie, Volume VIII, Georg Thieme Verlag Stuttgart (1952), 709, Volume IX (1955), 405). Also, for this purpose, the solvents and auxiliary bases indicated as examples above can be used.

Nucleofuge-substituted, i.e., alkyl side chains of tetraphenylporphyrins substituted, e.g., by chlorine, bromine, iodine, toluenesulfonate, can be converted, e.g., in a way known in the art to nitrile chains and the latter to carboxy-substituted side chains (Houben-Weyl, Methoden der organischen Chemie, Volume VIII, Georg Thieme Verlag Stuttgart (1952) 265).

The neutralization of the complexes optionally resulting as acids optionally takes place with the help of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or of amides of originally neutral or acidic amino acids.

For the production of neutral complex compounds, for example, enough of the desired bases can be added to the metalloporphyrins, isolated as (oligo-)acids, in aqueous solution or suspension that the neutral point is reached. The obtained solution can then be evaporated to dryness in a vacuum. Often, it is advantageous to precipitate the formed neutral salts by the addition of water-miscible solvents, such as, for example, lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates.

In the case of using complex compounds containing radioisotopes, their production can be performed according to the methods described in "Radiotracers for Medical Applications," Volume 1, CRC Press, Boca Raton, Fla.

The production of the pharmaceutical agents according to the invention also takes place in a way known in the art, by the complex compounds according to the invention being suspended or dissolved in aqueous medium—optionally by the addition of the additives usual in galenicals—then the suspension or solution optionally being sterilized. Suitable additives are, for example, physiologically harmless buffers (such as, for example, tromethamine), small additions of complexing agents (such as, for example, diethylenetriaminepentaacetic acid) or, if necessary, electrolytes, such as, for example, sodium chloride or, if necessary, antioxidants, such as, for example, ascorbic acid. If suspensions or solutions of the agents in water or physiological salt solution according to the invention are desired for enteral administration or other purposes, they are mixed with one or more adjuvant(s) usual in galenicals (for example, methyl cellulose, lactose, mannitol) and/or surfactant(s) (for example, lecithins, Tween®, Myrj®, taurocholate) and/or flavoring substance(s) for taste correction (for example, ethereal oils). They can also be used in the form of capsules in the case of oral administration or as liposomes.

Special care must be taken to perform the complexing, so that the metalloporphyrins and their solutions according to the invention are virtually free of noncomplexed metal ions having a toxic effect.

This can be assured, for example, with the help of color indicators, such as xylenol orange, by control titrations during the production process. The invention therefore also relates to the process for the production of complex compounds and their salts. A purification of the isolated complex salt remains as a last safety measure. To avoid undesirable photoreactions of porphyrins, the compounds and agents according to the invention should be stored and handled as much as possible with exclusion of light.

The pharmaceutical agents according to the invention preferably contain 20 μmol/L to 200 mmol/L of the complex salt and are generally dosed in amounts of 0.01 μmol to 2.0 mmol/kg of body weight, and the preferred dose for NMR diagnosis is 0.01–0.50 mmol/kg of body weight. The complex compounds according to the invention are intended for enteral and parenteral administration and are used 1. for NMR diagnosis in the form of their complexes with the ions of elements with atomic numbers 21–29, 42, 44 and 58–70;

2. for radiodiagnosis and radiotherapy in the form of their complexes with the radioisotopes of elements with atomic numbers 27, 29–32, 38–39, 42–51, 62, 64, 70, 75, 77, 82 and 83.

The water solubility of the agents according to the invention makes it possible to produce concentrated solutions, so that the volume load of the circulatory system is kept within reasonable limits and the dilution is balanced by bodily fluid. Further, the agents according to the invention exhibit not only high stability in vitro, but also surprisingly high stability in vivo, so that a release or an exchange of the ions—toxic in themselves—not covalently bound to the complexes takes place within the time in which the new contrast media are completely excreted again, only extremely slowly.

Further, the complex compounds according to the invention advantageously can be used as susceptibility reagents and as shift reagents for in vivo NMR spectroscopy.

The agents according to the invention are also suitable as radiodiagnostic agents because of their advantageous radioactive properties and the good stability of the complex compounds contained in them. Details of their use and dosage are described, e.g., in "Radiotracers for Medical Applications," CRC Press, Boca Raton, Fla. Another imaging method with radioisotopes is positron emission tomography, which uses positron-emitting isotopes, e.g., $^{43}$Sc, $^{44}$Sc, $^{52}$Fe, $^{55}$Co and $^{68}$Ga (Heis, W. D. Phelps, M. E. Positron Emission Tomography of Brain, Springer Verlag Berlin, Heidelberg, N.Y., 1983).

The compounds according to the invention can also be used in radioimmunotherapy. This is distinguished from the corresponding diagnosis only by the amount and type of radioactive isotope used. In this case, the object is the destruction of tumor cells by high-energy shortwave radiation with a smallest possible range of action. The specificity of the complex according to the invention is of decisive importance here, since unspecifically located complexes result in the destruction of healthy tissue.

On the target site, the metal ion selected because of its cell-killing property emits rays which lethally damage the cells. Suitable β-emitting ions are, for example, $^{46}$Sc, $^{47}$Sc, $^{48}$Sc, $^{72}$Ga and $^{73}$Ga. Suitable α-emitting ions exhibiting small half-lives are, for example, $^{211}$Bi, $^{212}$Bi, $^{213}$Bi and $^{214}$Bi, and $^{212}$Bi is preferred. A suitable ion emitting photons and electrons is $^{158}$Gd, which can be obtained from $^{157}$Gd by neutron capture.

In the in vivo administration of therapeutic agents according to the invention, the latter can be administered together with a suitable vehicle, such as, for example, serum or physiologically common salt solution, and together with another protein, such as, for example, human serum albumin. In this case, the dosage is dependent on the type of cellular impairment and the metal ion used.

In general, it has been possible to synthesize new complex compounds that open up new possibilities for diagnosis and therapy. The examples below are used for a more detailed explanation of the object of the invention without intending to be limited to this object.

EXAMPLE 1 a) 5,10,15,20-Tetrakis-{4-[(1-methylethyl)-oxycarbonylmethoxy]-phenyl}-porphyrin 3.21 g (4.73 mmol) of 5,10,15,20-tetrakis-(4-hydroxyphenyl)-porphyrin [CA RN 51094-17-8] is dissolved in 250 ml of anhydrous dimethylformamide and mixed with 13.07 g (94.60 mmol) of potassium carbonate and 3.14 g (18.92 mmol) of potassium iodide. 17.13 g (94.60 mmol) of bromoacetic acid isopropyl ester is instilled in the suspension that is stirred under argon at 21° C. After 24 hours of stirring with exclusion of light, the suspension is filtered, the filtrate is largely concentrated by evaporation in a vacuum, mixed with 250 ml of dichloromethane and shaken out twice with water. The organic phase is dried on anhydrous calcium chloride, filtered and concentrated by evaporation. The residue is chromatographed on silica gel 60 (Merck), the eluate of the product fractions that is concentrated by evaporation is recrystallized from dichloromethane/isopropanol.

Yield: 4.51 g (88% of theory) of violet crystals

Analysis (relative to anhydrous substance): C 71.23 H 5.79 N 5.19 O 17.79 Cld. C 71.11 H 5.81 N 5.08 b) Manganese(III)-{5,10,15,20-tetrakis-[4-[(1-methylethyl)-oxycarbonylmethoxy]-phenyl]-porphyrin}-acetate 3.04 g (2.82 mmol) of the compound produced under Example 1a and 15.00 g of manganese(II) acetate tetrahydrate are refluxed in 280 ml of acetic acid for one hour. It is evaporated to dryness in a vacuum, the residue is taken up in 250 ml of dichloromethane and shaken out once with water and twice with saturated aqueous sodium bicarbonate solution. The organic phase is dried on anhydrous magnesium sulfate, filtered and concentrated by evaporation. The residue is recrystallized from isopropanol.

Yield: 3.06 g (91% of theory) of dark green crystals

Analysis (relative to anhydrous substance): C 66.55 H 5.33 Mn 4.61 N 4.70 O 18.80 Cld. C 66.38 H 5.24 Mn 4.59 N 4.54 c) Manganese(III)-{5,10,15,20-tetrakis-[4-(carboxymethoxy)-phenyl]-porphyrin}-chloride 2.52 g (2.12 mmol) of the compound produced under Example 1b is dissolved in 250 ml of tetrahydrofuran. 250 ml of 2 n sodium hydroxide solution is added and refluxed until saponification is completed (about one hour). Then, the organic solvent is largely evaporated in a vacuum and by adjustment to pH 1–2, the product is precipitated by the addition of semiconcentrated hydrochloric acid. The title compound is suctioned off, washed with water and dried in a vacuum.

Yield: 2.05 g (97% of theory) of dark green crystals

Analysis (relative to anhydrous substance): C 62.50 H 3.63 Cl 13.55 Mn 5.50 N 5.61 O 19.21 Cld. C 62.41 H 3.58 Cl 13.71 Mn 5.44 N 5.42 d) Manganese(III)-{5,10,15,20-tetrakis-[4-(carboxylatomethoxy)-phenyl]-porphyrin}-chloride, tetrasodium salt 1.52 g (1.52 mmol) of the compound produced under Example 1c) is refluxed in 250 ml of 2 n sodium hydroxide solution for 30 minutes. After cooling, it is adjusted to pH 9 with semiconcentrated hydrochloric acid, the poorly soluble tetrasodium salt is filtered off, washed with water and dried in a vacuum.

Yield: 1.47 g (89% of theory) of dark green crystals

Analysis (relative to anhydrous substance): C 57.45 H 2.97 Cl 13.26 Mn 5.05 N 5.15 Na 8.46 O 17.66 Cld. C 57.38 H 2.88 Cl 13.47 Mn 4.97 N 5.03 Na 8.71

EXAMPLE 2 a) 5,10,15,20-Tetrakis-{3-[1-(methylethyl-oxycarbonylmethoxy]-phenyl}-porphyrin 4.12 g (6.07 mmol) of 5,10,15,20-tetrakis-(3-hydroxyphenyl)-porphyrin [CA RN 22112-79-4] is dissolved in 250 ml of anhydrous N,N-dimethylformamide and mixed with 16.78 g (121.4 mmol) of potassium carbonate and 4.03 g (24.28 mmol) of potassium iodide. 21.98 g (121.4 mmol) of bromoacetic acid isopropyl ester is instilled in the suspension that is stirred under argon at 21° C. After 24 hours of stirring with exclusion of light, the suspension is filtered, the filtrate is largely concentrated by evaporation in a vacuum, mixed with 250 ml of dichloromethane and shaken out twice with water. The organic phase is dried on anhydrous magnesium sulfate, filtered and concentrated by evaporation. The residue is chromatographed on silica gel 60, the eluate that is concentrated by evaporation is recrystallized from isopropanol.

Yield: 5.44 g (83% of theory) of violet crystals

Analysis (relative to anhydrous substance): C 71.23 H 5.79 N 5.19 O 17.79 Cld. C 71.08 H 5.85 N 5.12 b) Manganese(III)-{5,10,15,20-tetrakis-[3-[(1-methylethyl)-oxycarbonylmethoxy]-phenyl]-porphyrin}-acetate 5.09 g (4.72 mmol) of the compound produced under Example 2a and 25.00 g of manganese(II) acetate tetrahydrate are refluxed in 200 ml of acetic acid for one hour. It is evaporated to dryness in a vacuum, the residue is taken up in 250 ml of dichloromethane and shaken out once with water and twice with saturated aqueous sodium bicarbonate solution. The organic phase is dried on anhydrous magnesium sulfate, filtered and concentrated by evaporation. The residue is recrystallized from water/isopropanol.

Yield: 5.00 g (89% of theory) of dark green crystals

Analysis (relative to anhydrous substance): C 66.55 H 5.33 Mn 4.61 N 4.70 O 18.80 Cld. C 66.35 H 5.41 Mn 4.72 N 4.61 c) Manganese(III)-{5,10,15,20-tetrakis-[3-(carboxymethoxy)-phenyl]-porphyrin}-chloride 4.08 g (3.43 mmol) of the compound produced under Example 2b is dissolved in 200 ml of tetrahydrofuran. 200 ml of 2 n aqueous sodium hydroxide solution is added and refluxed until saponification is completed (about 1 hour). Then, the organic solvent is largely evaporated in a vacuum and by adjustment to pH 1–2, the product is precipitated by the addition of semiconcentrated hydrochloric acid. The title compound is suctioned off, washed with water and dried in a vacuum.

Yield: 3.18 g (93% of theory) of dark green crystals

Analysis (relative to anhydrous substance):
C 62.50 H 3.63 Cl 3.55 Mn 5.50 N 5.61 O 19.21 Cld.
C 62.32 H 3.75 Cl 3.81 Mn 5.41 N 5.36 d) Manganese(III)-{5,10,15,20-tetrakis-[3-(carboxylatomethoxy)-phenyl]-porphyrin}-chloride, tetrasodium salt 3.04 g (3.04 mmol) of the compound produced under 2c is dissolved in 60.84 ml of 0.20 n aqueous sodium hydroxide solution in an ultrasonic bath. The solution is then freeze-dried.

Yield: 3.31 g (100% of theory) of green lyophilizate

Analysis (relative to anhydrous substance):
C 57.45 H 2.97 Cl 3.26 Mn 5.05 N 5.15 Na 8.46 O 17.66 Cld.
C 57.57 H 3.14 Cl 3.43 Mn 4.92 N 5.06 Na 8.55

EXAMPLE 3 a) Zn(II)-[5,10,15,20-tetrakis-{2-[(1-methylethyl)-oxycarbonylmethyl]-phenyl}-porphyrin], (4 atropo-isomers)

33.34 g (0.150 mol) of (2-formylphenoxy)-acetic acid isopropyl ester (CA RN 51336-26-6) is dissolved in 350 ml of propionic acid and mixed with 8.78 g (0.040 mol) of zinc(II) acetate dihydrate. The solution is heated to 60° C. and 10.06 g (0.150 mol) of pyrrole is instilled slowly. Then, the temperature is increased to 110° C. and stirring is allowed to continue for one hour. After cooling, it is completely concentrated by evaporation in a vacuum, the residue is taken up in dichloromethane and shaken out once with water and twice with aqueous sodium bicarbonate solution. The organic phase is dried on anhydrous magnesium sulfate, filtered, largely concentrated by evaporation and chromatographed on silica gel 60 (Merck) with dichloromethane/methanol. After the concentration by evaporation, a mixture of four atropo-isomers each of the zinc complex and the free ligand is obtained. The mixture is dissolved in 100 ml of dichloromethane, mixed with 10 ml of concentrated methanolic zinc(II) acetate dihydrate solution and refluxed for 30 minutes. After cooling, additional dichloromethane is added, shaken out twice with water, the organic phase is separated, the latter is dried on magnesium sulfate, filtered and concentrated by evaporation. The residue is recrystallized from water/isopropanol.

Yield: 10.41 g (24% of theory) of dark violet crystals

Analysis (relative to anhydrous substance): C 67.28 H 5.29 N 4.90 O 16.80 Zn 5.72 Cld. C 67.11 H 5.48 N 4.67 Zn 5.60 b) 5,10,15,20-Tetrakis-{2-[(1-methylethyl)-oxycarbonylmethoxy]-phenyl}-porphyrin (4 atropo-isomers)

5.02 g (4.39 mmol) of the compound produced under Example 2a) is stirred in a mixture of 60 ml of trifluoroacetic acid, 10 ml of isopropanol and 10 ml of water for about one hour at 20° C. Then, the solution is brought to pH 7 at 0° C. with saturated aqueous sodium bicarbonate solution and shaken out with dichloromethane. After drying the organic phase on anhydrous magnesium sulfate, filtration and concentration by evaporation of the filtrate in a vacuum, the resulting residue is recrystallized from isopropanol.

Yield: 4.22 g (89% of theory) of violet crystals

Analysis (relative to anhydrous substance): C 71.23 H 5.79 N 5.19 O 17.79 Cld. C 70.96 H 5.88 N 5.02 c) Manganese(III)-[5,10,15,20-tetrakis-{2-[(1-methylethyl)-oxycarbonylmethoxy]-phenyl}-porphyrin]-acetate (4 atropo-isomers)

The production of the title compound can take place analogously to the method, described in Example 1b or 2b, starting from 3b, but also directly from the zinc complex described under Example 3a:

4.27 g (3.74 mmol) of the compound described under Example 3a is refluxed with 250 ml of acetic acid for one hour after the addition of 20.00 g of manganese(II) acetate. It is evaporated to dryness in a vacuum, the residue is taken up in 300 ml of dichloromethane and shaken out once with water and twice with saturated, aqueous sodium bicarbonate solution. The organic phase is dried on anhydrous magnesium sulfate, filtered and concentrated by evaporation. The residue is recrystallized from isopropanol/water.

Yield: 3.74 g (84% of theory) of dark green crystals

Analysis (relative to anhydrous substance): C 66.55 H 5.33 Mn 4.61 N 4.70 O 18.80 C 66.42 H 5.56 Mn 4.73 N 4.45 d) Manganese(III)-{5,10,15,20-tetrakis-(2-(carboxymethoxy)-phenyl]-porphyrin}-chloride, (4 atropo-isomers)

3.11 g (2.61 mmol) of the compound produced under Example 3c is dissolved in 250 ml of tetrahydrofuran. 250 ml of 2 n aqueous sodium hydroxide solution is added and refluxed until saponification is completed (about one hour). Then, the organic solvent is largely evaporated in a vacuum and by adjustment to pH 1–2, the product is precipitated by the addition of semiconcentrated aqueous hydrochloric acid. The title compound is suctioned off, washed with water and dried in a vacuum.

Yield: 2.30 g (88% of theory) of dark green crystals

Analysis (relative to anhydrous substance): C 62.50 H 3.63 Cl 13.55 Mn 5.50 N 5.61 O 19.21 C 62.29 H 3.75 Cl 3.67 Mn 5.53 N 5.38

EXAMPLE 4 a) Zinc(II)-{5,10,15,20-tetrakis-[3,4-bis-(ethoxycarbonylmethoxy)-phenyl]-porphyrin}

10.11 g (32.58 mmol) of 3,4-bis-(ethoxycarbonylmethoxy)-benzaldehyde (CA RN 119309-58-9) and 1.79 g (8.15 mmol) of zinc acetate dihydrate are dissolved in 100 ml of propionic acid. 2.19 g (32.58 mmol) of pyrrole is slowly instilled in the solution stirred at 80° C., stirring of the now dark reaction mixture is allowed to continue for one hour at 100° C. After cooling, it is completely concentrated by evaporation in a vacuum, the residue is taken up in dichloromethane and shaken out once with water and twice with aqueous sodium bicarbonate solution. The organic phase is dried on anhydrous magnesium sulfate, filtered, largely concentrated by evaporation and chromatographed on silica gel 60 (Merck) with dichloromethane/ methanol. After the concentration by evaporation, a mixture of the zinc complex and the free ligand is obtained. The mixture is dissolved in 50 ml of dichloromethane, mixed with 5 ml of concentrated methanolic zinc acetate-dihydrate solution and refluxed for 30 minutes. After cooling, additional methylene chloride is added, shaken out twice with water, the organic phase is separated, the latter is dried on magnesium sulfate, filtered and concentrated by evaporation. The residue is recrystallized from water/isopropanol.

Yield: 2.08 g (17% of theory) of dark violet crystals

Analysis (relative to anhydrous substance): C 61.07 H. 5.12 N 3.75 O 25.69 Zn 4.37 Cld. C 60.84 H 5.27 N 3.68 Zn 4.09 b) 5,10,15,20-Tetrakis-[3,4-bis-(ethoxycarbonylmethoxy)-phenyl]-porphyrin 0.51 g (0.34 mmol) of the compound produced under Example 4a) is stirred in a mixture of 10 ml of trifluoroacetic acid, 1 ml of ethanol and 1 ml of water for about one hour at 20° C. Then, the solution is brought to pH 7 with saturated aqueous sodium bicarbonate solution at 0° C. and shaken out with dichloromethane. After drying the organic phase on anhydrous magnesium sulfate, filtration and concentration by evaporation of the filtrate in a vacuum, the residue is recrystallized from isopropanol.

Yield: 0.41 g (84% of theory) of violet crystals

Analysis (relative to anhydrous substance): C 63.77 H 5.49 N 3.91 O 26.82 Cld. C 63.62 H 5.54 N 3.84 c) Manganese(III)-{5,10,15,20-tetrakis-[3,4-bis-(ethoxycarbonylmethoxy)-phenyl]-porphyrin}-acetate 1.34 g (0.90 mmol) of the compound produced under Example 4a) and 6.70 g of manganese(II) acetate tetrahydrate are refluxed in 125 ml of acetic acid for one hour. It is evaporated to dryness in a vacuum, the residue is taken up in 125 ml of dichloromethane and shaken out once with water, twice with saturated aqueous sodium bicarbonate solution. The organic phase is dried on anhydrous magnesium sulfate, filtered and concentrated by evaporation. The residue is recrystallized from isopropanol/water.

Yield: 1.21 g (89% of theory) of dark green crystals

Analysis (relative to anhydrous substance): C 60.06 H 5.04 Cl 2.33 Mn 3.61 N 3.69 O 25.26 Cld. C 59.82 H 5.10 Cl 2.14 Mn 3.39 N 3.48 d) Manganese(III)-{5,10,15,20-tetrakis-[3,4-bis-(carboxymethoxy)-phenyl]-porphyrin}-chloride 1.00 g (0.66 mmol) of the compound produced under Example 4c) is dissolved in 50 ml of tetrahydrofuran. 50 ml of 2 n aqueous sodium hydroxide solution is added and refluxed until saponification is completed (about one hour). Then, the organic solvent is largely evaporated in a vacuum and the product is precipitated by the addition of semiconcentrated aqueous hydrochloric acid and adjustment to pH 1–2. The title compound is suctioned off, washed with water and dried in a vacuum.

Yield: 0.84 g (98% of theory) of dark green crystals

Analysis (relative to anhydrous substance): C 55.63 H 3.42 Cl 2.74 Mn 4.24 N 4.33 O 29.64 Cld. C 55.74 H 3.58 Cl 2.92 Mn 3.98 N 4.12 e) Manganese(III)-{5,10,15,20-tetrakis-[3,4-bis-(carboxylatomethoxy)-phenyl]-porphyrin}-chloride, octasodium salt 0.61 g (0.47 mmol) of the compound produced under Example 4d) is dissolved in 2.35 ml of 0.20 n aqueous sodium hydroxide solution. The solution is then freeze-dried.

Yield: 0.69 g (100% of theory) of green lyophilizate

Analysis (relative to anhydrous substance): C 48.98 H 2.47 Cl 2.41 Mn 3.72 N 3.81 Na 12.50 O 26.10 Cld. C 48.87 H 2.51 Cl 2.56 Mn 3.57 N 3.72 Na 12.72

EXAMPLE 5 a) 5,10,15,20-Tetrakis-(3-acetylaminophenyl)-porphyrin 16.32 g (0.10 mol) of 3-acetylaminobenzaldehyde (EMS-Dottikon AG) is dissolved in 300 ml of propionic acid and the solution is heated to 60° C. 6.71 g (0.10 mol) of pyrrole is instilled slowly and the dark solution is stirred for one hour at 110° C. After cooling, it is completely concentrated by evaporation in a vacuum, and the residue is recrystallized from pyridine/diethyl ether.

Yield: 8.43 g (40% of theory) of violet crystals

Analysis (relative to anhydrous substance): C 74.09 H 5.02 N 13.29 O 7.59 Cld. C 73.88 H 5.11 N 13.14 b) 5,10,15,20-Tetrakis-{{N-acetyl-N-[(1-methylethyl)-oxycarbonylmethyl]}-3-aminophenyl}-porphyrin 7.21 g (8.55 mmol) of the compound produced under Example 5a) is dissolved and mixed with 23.64 g (171.1 mmol) of potassium carbonate and 5.68 g (34.2 mmol) of potassium iodide. 30.97 g (171.1 mmol) of bromoacetic acid isopropyl ester is instilled in the solution stirred under argon at 21° C. After 36 hours of stirring with exclusion of light, the suspension is filtered, the filtrate is largely concentrated by evaporation in a vacuum, mixed with 500 ml of dichloromethane and shaken out twice with water. The organic phase is dried on anhydrous magnesium sulfate, filtered and concentrated by evaporation. The residue is chromatographed on silica gel 60 (Merck), the eluate that is concentrated by evaporation is recrystallized from isopropanol.

Yield: 6.59 g (62% of theory) of violet crystals

Analysis (relative to anhydrous substance):

C 69.55 H 6.00 N 9.01 O 15.44 Cld.

C 69.71 H 6.09 N 8.86 c) Manganese(III)-{5,10,15,20-tetrakis-{{N-acetyl-N-[(1-methylethyl)-oxycarbonylmethyl]}-3-aminophenyl}-porphyrin}-acetate 6.07 g (4.88 mmol) of the compound produced under Example 5b) and 30.0 g of manganese(II) acetate tetrahydrate are refluxed in 250 ml of acetic acid for one hour. It is evaporated to dryness in a vacuum, the residue is taken up in 300 ml of dichloromethane and shaken out once with water and twice with saturated, aqueous sodium bicarbonate solution. The organic phase is dried on anhydrous magnesium sulfate, filtered and concentrated by evaporation. The residue is recrystallized from aqueous isopropanol.

Yield: 5.98 g (90% of theory) of dark green crystals

Analysis (relative to anhydrous substance): C 65.58 H 5.58 Mn 4.05 N 8.27 O 16.53 Cld. C 65.39 H 5.67 Mn 4.11 N 8.18 d) Manganese(III)-{5,10,15,20-tetrakis-[(N-acetyl-N-carboxymethyl)-aminophenyl]-3-porphyrin}-chloride 4.67 g (3.45 mmol) of the compound produced under Example 5c) is dissolved in 200 ml of tetrahydrofuran. 200 ml of 2 n aqueous sodium hydroxide solution is added and refluxed until saponification is completed (about one hour). Then, the organic solvent is largely evaporated in a vacuum, and by adjustment to pH 1–2, the product is precipitated by the addition of semiconcentrated aqueous hydrochloric acid. The title compound is suctioned off, washed with water and dried in a vacuum.

Yield: 3.89 g (97% of theory) of dark green crystals

Analysis (relative to anhydrous substance): C 61.94 H 4.16 Cl 3.05 Mn 4.72 N 9.63 O 16.50 Cld. C 61.82 H 4.25 Cl 3.31 Mn 4.66 N 9.53 e) Manganese(III)-{5,10,15,20-tetrakis-[(N-acetyl-N-carboxylatomethyl)-3-aminophenyl]-porphyrin}-chloride, tetrasodium salt 2.57 g (2.21 mmol) of the compound produced under Example 2d) is dissolved in 44.18 ml of 0.20 n aqueous sodium hydroxide solution in an ultrasonic bath. The solution is then freeze-dried.

Yield: 2.76 g (100% of theory) of dark green lyophilizate

Analysis (relative to anhydrous substance): C 57.59 H 3.54 Cl 2.83 Mn 4.39 N 8.95 Na 7.35 O 15.34 Cld. C 57.38 H 3.77 Cl 2.95 Mn 4.27 N 8.76 Na 7.51

EXAMPLE 6 a) 5,10,15,20-Tetrakis-[3-(methoxycarbonylmethyl)-phenyl]-porphyrin 17.82 g (0.10 mol) of (3-formylphenyl)-acetic acid methyl ester (B RN 3231441) is dissolved in 300 ml of propionic acid and the solution is heated to 60° C. 6.71 g (0.10 mol) of pyrrole is instilled slowly and the dark solution is stirred for 1 hour at 110° C. After cooling, it is completely concentrated by evaporation in a vacuum, the residue is taken up in dichloromethane and shaken out with saturated aqueous sodium bicarbonate solution. After the drying of the organic phase on sodium sulfate, it is filtered and concentrated by evaporation, and the residue is chromatographed on silica gel 60 (Merck) with dichloromethane/methanol. The residue of the product fractions that are concentrated by evaporation is recrystallized from isopropanol.

Yield: 6.10 g (27% of theory)

Analysis (relative to anhydrous substance): C 74.49 H 5.13 N 6.20 O 14.17 Cld. C 74.61 H 5.27 N 6.14 b) Manganese(III)-{5,10,15,20-tetrakis-[3-(methoxycarbonylmethyl)-phenyl]-porphyrin}-acetate 5.78 g (6.40 mmol) of the compound produced under Example 6a) and 25 g of manganese(II) acetate tetrahydrate are stirred in 250 ml of acetic acid for 3 hours at 80° C. It is evaporated to dryness in a vacuum, the residue is taken up in 300 ml of dichloromethane and shaken out once with water and twice with saturated aqueous sodium bicarbonate solution. The organic phase is dried on anhydrous magnesium sulfate, filtered and concentrated by evaporation. The residue is recrystallized from aqueous methanol.

Yield: 5.65 g (87% of theory) of dark green crystals

Analysis (relative to anhydrous substance): C 68.64 H 4.67 Mn 5.41 N 5.52 O 15.76 Cld. C 68.53 H 5.79 Mn 5.58 N 5.42 c) Manganese(III)-{5,10,15,20-tetrakis-[3-(carboxymethyl)-phenyl]-porphyrin}-chloride 4.28 g (4.22 mmol) of the compound produced under Example 6b) is dissolved in 200 ml of tetrahydrofuran. 200 ml of 2 n aqueous sodium hydroxide solution is added and refluxed until saponification is completed (about one hour). Then, the organic solvent is largely evaporated in a vacuum and the product is precipitated at pH 1–2 by the addition of semiconcentrated aqueous hydrochloric acid. The title compound is suctioned off, washed with water and dried in a vacuum.

Yield: 3.75 g (95% of theory) of dark green crystals

Analysis (relative to anhydrous substance): C 66.78 H 3.88 Cl 3.79 Mn 5.87 N 5.99 O 13.69 C 66.77 H 4.00 Cl 3.91 Mn 5.73 N 5.92

EXAMPLE 7 a) 5,10,15,20-Tetrakis-{3-[2-(ethoxycarbonyl)-ethyl]-phenyl}-porphyrin 20.62 g (0.10 mol) of 3-{3-formylphenyl)-propionic acid ethyl ester (CARN 110114-05-1) is dissolved in 300 ml of propionic acid and the solution is heated to 60° C. 6.71 g (0.10 mol) of pyrrole is slowly instilled and the dark solution is stirred for 1 hour at 110° C. After cooling, it is completely concentrated by evaporation in a vacuum, the residue is taken up in dichloromethane and shaken out with saturated aqueous sodium bicarbonate solution. After the drying of the organic phase on sodium sulfate, it is filtered and concentrated by evaporation, and the residue is chromatographed on silica gel 60 (Merck) with dichloromethane/ethanol. The residue of the product fractions that are concentrated by evaporation is recrystallized from isopropanol.

Yield: 8.12 g (32% of theory) of violet crystals

Analysis (relative to anhydrous substance): C 75.72 H 6.16 N 5.52 O 12.61 Cld. C 75.81 H 6.09 N 5.57 b) Manganese(III)-{5,10,15,20-tetrakis-{3-[2-(ethoxycarbonyl)-ethyl]-phenyl}-porphyrin}-acetate 7.32 g (7.21 mmol) of the compound produced under Example 7a) and 28 g of manganese(II) acetate tetrahydrate are stirred in 250 ml of acetic acid for 3 hours at 80° C. It is concentrated by evaporation in a vacuum, the residue is taken up in 300 ml of dichloromethane and shaken out once with water and twice with saturated, aqueous sodium bicarbonate solution. The organic phase is dried on anhydrous sodium sulfate, filtered and concentrated by evaporation. The residue is recrystallized from aqueous ethanol.

Yield: 7.64 g (94% of theory) of dark green crystals

Analysis (relative to an anhydrous substance): C 70.33 H 5.63 Mn 4.87 N 4.97 O 14.19 Cld. C 70.18 H 5.71 Mn 4.80 N 4.82 c) Manganese(III)-{5,10,15,20-tetrakis-[3-(2-carboxyethyl)-phenyl]-porphyrin}-chloride 6.81 g (6.04 mmol) of the compound produced under Example 7b is dissolved in 200 ml of tetrahydrofuran. 200 ml of 2 n aqueous sodium hydroxide solution is added and refluxed until saponification is completed (about one hour). Then, the organic solvent is largely evaporated in a vacuum and the product is precipitated at pH 1–2 by the addition of semiconcentrated hydrochloric acid. The title compound is suctioned off, washed with water and dried in a vacuum.

Yield: 5.81 g (97% of theory) of dark green crystals

Analysis (relative to an anhydrous substance): C 67.85 H 4.47 Cl 3.58 Mn 5.54 N 5.65 O 12.91 Cld. C 67.69 H 4.53 Cl 3.72 Mn 5.38 N 5.52

EXAMPLE 8 a) 2-{N,N-Bis-[(1-methylethyl)-oxycarbonylmethyl]-3-aminophenyl}-1,3-dioxolan 165.19 g (1.00 mol) of 2-(3-aminophenyl)-1,3-dioxolan (CA 108 (15): 131815 r), 156.35 g (3.00 mol) of pulverized potassium hydroxide and 11.39 g (0.05 mol) of benzyltriethylammonium chloride are vigorously mechanically stirred under argon and heated to 80° C. 543.09 g (3.00 mol) of bromoacetic acid isopropyl ester is instilled in the suspension and the reaction mixture is stirred for about 8 hours at 80° C. Then, it is filtered, the filtrate is shaken out several times with concentrated aqueous sodium bicarbonate solution, the organic phase is dried on anhydrous magnesium sulfate, filtered and concentrated by evaporation in a vacuum. The residue is chromatographed on silica gel 60 (Merck) with methylene chloride/methanol. After concentration by evaporation, the product fractions yield a colorless oil.

Yield: 288.69 g (79% of theory)

Analysis (relative to anhydrous substance): C 62.45 H 7.45 N 3.83 O 26.27 Cld. C 62.39 H 7.53 N 3.84 b) N,N-Bis-[(1-methylethyl)-oxycarbonylmethyl]-3-aminobenzaldehyde 200.00 g (0.55 mol) of the compound produced under Example 8a) is stirred at 50° C. under argon in 1 l of a 1:1 mixture of acetone and 2 n aqueous hydrochloric acid until the reaction is completed. Then, it is concentrated by evaporation in a vacuum, the residue is taken up in dichloromethane and shaken out twice with saturated aqueous sodium bicarbonate solution. The organic phase is dried on anhydrous magnesium sulfate, filtered and concentrated by evaporation in a vacuum. The product is obtained as oily residue.

Yield: 160.06 g (91% of theory)

Analysis (relative to anhydrous substance): C 63.54 H 7.21 N 4.36 O 24.89 Cld. C 63.49 H 7.47 N 4.22 c) 5,10,15,20-Tetrakis-{N,N-bis-[(1-methylethyl)-oxycarbonylmethyl]-3-aminophenyl}-porphyrin 32.14 g (0.10 mol) of the compound produced under Example 8b is dissolved in 400 ml of propionic acid. The solution is heated to 60° C., 6.71 g (0.10 mol) of pyrrole is slowly instilled, and the dark solution is stirred for 1 hour at 110° C. After cooling, it is completely concentrated by evaporation in a vacuum, the residue is taken up with dichloromethane and shaken out with saturated aqueous sodium bicarbonate solution. After the drying of the organic phase on sodium sulfate, it is filtered, concentrated by evaporation and the residue is chromatographed on silica gel 60 (Merck) with dichloromethane/methanol. The residue of the product fractions that are concentrated by evaporation is recrystallized from aqueous isopropanol.

Yield: 9.22 g (25% of theory) of violet crystals

Analysis (relative to anhydrous substance): C 68.37 H 6.69 N 7.59 O 17.35 Cld. C 68.44 H 6.52 N 7.63 d) Manganese(III)-{5,10,15,20-tetrakis-{N,N-bis-[(1-methylethyl)-oxycarbonylmethyl]-3-aminophenyl}-porphyrin}-acetate 8.71 g (5.90 mmol) of the compound produced under Example 8c) and 30 g of manganese(II) acetate tetrahydrate are stirred in 250 ml of acetic acid for 2 hours at 100° C. It is evaporated to dryness in a vacuum, the residue is taken up in methylene chloride and shaken out once with water and twice with saturated aqueous sodium bicarbonate solution. The organic phase is dried on anhydrous magnesium sulfate, filtered and concentrated by evaporation. The residue is recrystallized from aqueous isopropanol.

Yield: 8.81 g (94% of theory) of dark green crystals

Analysis (relative to anhydrous substance): C 65.06 H 6.28 Mn 3.46 N 7.06 O 18.14 Cld. C 64.87 H 6.42 Mn 3.37 N 6.91 e) Manganese(III)-{5,10,15,20-tetrakis-{N,N-bis-(carboxymethyl)-3-aminophenyl-porphyrin}-chloride 7.24 g (4.56 mmol) of the compound produced under Example 8d is dissolved in 200 ml of tetrahydrofuran. 200 ml of 2 n aqueous sodium hydroxide solution is added and refluxed until saponification is completed (about 1.5 hours). Then, the organic solvent is largely evaporated in a vacuum, and the product is precipitated at pH 1–2 by the addition of semiconcentrated aqueous hydrochloric acid. The title compound is suctioned off, washed with water and dried in a vacuum.

Yield: 5.49 g (98% of theory) of dark green crystals

Analysis (relative to anhydrous substance): C 58.71 H 3.94 Cl 2.89 Mn 4.48 N 9.13 O 20.85 Cld. C 58.55 H 3.99 Cl 2.96 Mn 4.31 N 9.06

EXAMPLE 9 a) 5,10,15,20-Tetrakis-[3-(2-methoxycarbonyl-2-hydroxyethoxy)-phenyl]-porphyrin 7.64 g (11.26 mmol) of 5,10,15,20-tetrakis-(3-hydroxyphenyl)-porphyrin [CA RN 22112-79-4] is suspended in 300 ml of water. 14.02 g (112.56 mmol) of β-chlorolactic acid (Sigma) is added and adjusted to pH 9–10 by instillation of 2 n sodium hydroxide solution. After 12 hours of stirring and argon at 40° C., the reaction product is precipitated by adjustment to pH 1–2 with aqueous hydrochloric acid. The precipitate is suctioned off, dried in a vacuum, and dissolved in a mixture of dichloromethane/methanol. Then, ethereal diazomethane solution is instilled with stirring at 20° C. until the reaction is completed, determined by thin-layer chromatography. The reaction mixture is freed from excess diazomethane by the addition of acetic acid and concentrated by evaporation in a vacuum, the residue is chromatographed on silica gel 60 (Merck) with dichloromethane/methanol. The product fractions are concentrated by evaporation, the residue is recrystallized from aqueous methanol.

Yield: 7.22 g (59% of theory) of violet crystals

Analysis (relative to anhydrous substance): C 66.29 H 5.01 N 5.15 O 23.55 Cld. C 66.14 H 5.24 N 5.03 b) Manganese(III)-{5,10,15,20-tetrakis-[3-(2-methoxycarbonyl-2-hydroxyethoxy)-phenyl]-porphyrin}-acetate 5.89 g (5.42 mmol) of the compound produced under Example 9a and 23.00 g of manganese(II) acetate tetrahydrate are stirred in 200 ml of acetic acid for 3 hours at 80° C. It is evaporated to dryness in a vacuum, the residue is taken up in dichloromethane and shaken out once with water and twice with saturated aqueous sodium bicarbonate solution. The organic phase is dried on anhydrous magnesium sulfate, filtered and concentrated by evaporation. The residue is recrystallized from aqueous methanol.

Yield: 5.39 g (83% of theory) of dark green crystals

Analysis (relative to anhydrous substance): C 62.10 H 4.62 Mn 4.58 N 4.67 O 24.02 Cld. C 62.23 H 4.57 Mn 4.44 N 4.52 c) Manganese(III)-{5,10,15,20-tetrakis-[3-(2-carboxy-2-hydroxyethoxy)-phenyl]-porphyrin}-chloride 4.74 g (3.95 mmol) of the compound produced under Example 9b is dissolved in 200 ml of tetrahydrofuran. 200 ml of 2 n aqueous sodium hydroxide solution is added and stirred until saponification is completed at 60° C. (about 3 hours). Then, the organic solvent is largely evaporated in a vacuum, and the product is precipitated at pH 1–2 by the addition of semiconcentrated hydrochloric acid. The title compound is suctioned off, washed with water and dried in a vacuum.

Yield: 3.89 g (88% of theory) of dark green crystals

Analysis (relative to anhydrous substance): C 60.09 H 3.96 Cl 3.17 Mn 4.91 N 5.01 O 22.87 Cld. C 59.87 H 4.08 Cl 3.24 Mn 4.81 N 4.83

EXAMPLE 10 a) 5,10,15,20-Tetrakis-{N-[(1-methylethyl)-oxycarbonylmethyl]-N-(p-toluenesulfonyl)-3-aminomethylphenyl}-porphyrin 1.98 g (1.13 mmol) of 5,10,15,20-tetrakis-[3-(p-toluenesulfonamidomethyl)-phenyl]-porphyrin [T. C. Bruice et al., J. Am. Chem. Soc. 1991, 113, 4208–4218] is dissolved in 20 ml of anhydrous N,N-dimethylformamide and mixed with 1.25 g (9.06 mmol) of potassium carbonate. 1.64 g (9.06 mmol) of bromoacetic acid isopropyl ester is instilled in the suspension that is stirred under argon at 21° C. After 24 hours of stirring with exclusion of light, the suspension is filtered, the filtrate is largely concentrated by evaporation in a vacuum, mixed with 50 ml of dichloromethane and shaken out twice with water. The organic phase is dried on anhydrous sodium sulfate, filtered and concentrated by evaporation. The residue is chromatographed on silica gel 60 (Merck), the eluate that is concentrated by evaporation is recrystallized from isopropanol.

Yield: 1.64 g (82% of theory) of violet crystals

Analysis (relative to anhydrous substance): C 65.96 H 5.65 N 6.41 O 14.64 S 7.34 Cld. C 65.84 H 5.79 N 6.40 S 7.16 b) Manganese(III)-{5,10,15,20-tetrakis-{N-[(1-methylethyl)-oxycarbonylmethyl]-N-(p-toluenesulfonyl)-3-aminomethylphenyl}-porphyrin}-acetate 1.47 g (0.84 mmol) of the compound produced under Example 10a and 8.00 g of manganese(II) acetate tetrahydrate are refluxed in 200 ml of acetic acid for one hour. It is evaporated to dryness in a vacuum, the residue is taken up in 50 ml of dichloromethane and shaken out once with water and twice with saturated aqueous sodium bicarbonate solution. The organic phase is dried on anhydrous magnesium sulfate, filtered and concentrated by evaporation. The residue is recrystallized from water/isopropanol.

Yield: 1.19 g (75% of theory) of dark green crystals

Analysis (relative to anhydrous substance): C 63.28 H 5.36 Mn 2.95 N 6.02 O 15.48 S 6.90 Cld. C 63.17 H 5.37 Mn 2.88 M 5.86 S 6.79 c) Manganese(III)-{5,10,15,20-tetrakis-[N-(carboxymethyl)-N-(p-toluenesulfony)-3-aminomethylphenyl]-porphyrin}-chloride 0.97 g (0.52 mmol) of the compound produced under Example 10b is dissolved in 50 ml of tetrahydrofuran. 100 ml of 2 n aqueous sodium hydroxide solution is added and refluxed until saponification is completed (about one hour). Then, the organic solvent is largely evaporated in a vacuum, and the product is precipitated at pH 1–2 by the addition of semiconcentrated aqueous salt. The title compound is suctioned off, washed with water and dried in a vacuum.

Yield: 0.86 g (99% of theory) of dark green crystals

Analysis (relative to anhydrous substance): C 60.48 H 4.35 Cl 2.13 Mn 3.29 N 6.72 O 15.35 S 7.69 C 60.51 H 4.47 Cl 2.43 Mn 3.08 N 6.49 S 7.51

EXAMPLE 11 a) 5,10,15,20-Tetrakis-[3-(3-phthalimidopropyloxy)-phenyl]-porphyrin 7.56 g (11.14 mmol) of 5,10,15,20-tetrakis-(3-hydroxyphenyl)-porphyrin [CARN 22112-79-4] is dissolved in 300 ml of anhydrous N,N-dimethylformamide and mixed with 30.79 g (222.8 mmol) of potassium carbonate and 7.40 g (44.55 mmol) of potassium iodide. 59.72 g (222.8 mmol) of N-(3-bromopropyl)-phthalimide is added to the suspension that is stirred under argon at 21° C. After 24 hours of stirring with exclusion of light, the suspension is filtered, the filtrate is largely concentrated by evaporation in a vacuum, mixed with dichloromethane and shaken out twice with water. The organic phase is dried on anhydrous magnesium sulfate, filtered and concentrated by evaporation, the residue is chromatographed on silica gel 60 (Merck) with dichloromethane/methanol. The product fractions are concentrated by evaporation, taken up in a little dichloromethane and the title compound is precipitated by the addition of diethyl ether.

Yield: 11.77 g (74% of theory) of violet crystals

Analysis (relative to anhydrous substance) C 74.04 H 4.66 N 7.85 O 13.45 Cld. C 74.21 H 4.49 N 7.84 b) 5,10,15,20-Tetrakis-[3-(3-aminopropyloxy)-phenyl]-porphyrin 10.09 g (7.07 mmol) of the compound produced under Example 11a is refluxed in 300 ml of pyridine after the addition of 3.54 g (70.68 mmol) of hydrazine hydrate until unblocking of the amino radical is completed (about 1 hour). Then, it is concentrated by evaporation in a vacuum, the residue is taken up in dichloromethane and shaken out several times with saturated aqueous or sodium bicarbonate solution. The organic phase is dried anhydrous magnesium sulfate, filtered and concentrated by evaporation. The residue is chromatographed on aluminum oxide 90 (Merck) with dichloromethane/methanol, the product fractions are concentrated by evaporation, the residue is taken up in a little dichloromethane, the title compound is precipitated and suctioned off by instillation of tert-butyl methyl ether.

Yield: 4.87 g (76% of theory)

Analysis (relative to anhydrous substance) C 74.15 H 6.44 N 12.35 O 7.05 Cld. C 74.94 H 6.41 N 12.28 c) 5,10,15,20-Tetrakis-[3-(N-acetyl-3-aminopropyloxy)-phenyl]-porphyrin 4.11 g (4.53 mmol) of the compound produced under Example 11b is stirred in 150 ml of a 1:1 mixture of pyridine and acetic anhydride for 8 hours under argon at 21° C. Then, it is concentrated by evaporation in a vacuum, the residue is taken up in dichloromethane and shaken out once with saturated aqueous sodium hydrogen sulfate solution and twice with saturated aqueous sodium bicarbonate solution. The organic phase is dried on magnesium sulfate, filtered, concentrated by evaporation and the residue is chromatographed on silica gel 60 (Merck) with dichloromethane/methanol. The product fractions that are concentrated by evaporation are recrystallized from isopropanol.

Yield: 3.95 g (81% of theory) of violet crystals

Analysis (relative to anhydrous substance) C 71.49 H 6.19 N 10.42 O 11.90 Cld. C 71.31 H 6.28 N 10.24 d) 5,10,15,20-Tetrakis-{3-{N-acetyl-N-[(1-methylethyl)-oxycarbonylmethyl]-3-aminopropyloxy}-phenyl}-porphyrin 3.57 g (3.32 mmol) of the compound produced under Example 11c is dissolved in 250 ml of anhydrous N,N-dimethylformamide and mixed with 9.18 g (66.4 mmol) of potassium carbonate and 2.20 g (13.3 mmol) of potassium iodide. 12.02 g (66.4 mmol) of bromoacetic acid isopropyl ester is instilled in the suspension that is stirred under argon at 21° C. After 24 hours with exclusion of light, the suspension is filtered, the filtrate is largely concentrated by evaporation in a vacuum, mixed with dichloromethane and shaken out twice with water. The organic phase is dried on anhydrous magnesium sulfate, filtered and concentrated by evaporation. The residue is chromatographed on silica gel 60 (Merck) with dichloromethane/methanol and the eluate that is concentrated by evaporation is recrystallized from isopropanol.

Yield: 3.43 g (70% of theory) of violet crystals

Analysis (relative to anhydrous substance) C 68.37 H 6.69 N 7.59 O 17.35 Cld. C 68.30 H 6.79 N 7.33 e) Manganese(III)-{5,10,15,20-tetrakis-{3-{N-acetyl-N-[(1-methylethyl)-oxycarbonylmethyl]-3-aminopropyloxy}-phenyl}-porphyrin}-acetate 3.01 g (2.04 mmol) of the compound produced under Example 11d and 15.00 g of manganese(II) acetate tetrahydrate are refluxed in 150 ml of acetic acid for one hour. It is evaporated to dryness in a vacuum, the residue is taken up in 200 ml of dichloromethane and shaken out once with water and twice with saturated aqueous sodium bicarbonate solution. The organic phase is dried on anhydrous magnesium sulfate, filtered and concentrated by evaporation. The residue is recrystallized from water/isopropanol.

Yield: 2.75 g (85% of theory) of dark green crystals

Analysis (relative to anhydrous substance): C 65.06 H 6.28 Mn 3.46 N 7.06 O 18.14 Cld. C 65.12 H 6.21 Mn 3.39 N 7.14 f) Manganese(III)-{5,10,15,20-tetrakis-[3-(N-acetyl-N-carboxylmethyl-3-aminopropyloxy)-phenyl]-porphyrin}-chloride 2.68 g (1.69 mol) of the compound produced under Example 11e is dissolved in 150 ml of tetrahydrofuran. 150 ml of 2 n aqueous sodium hydroxide solution is added and refluxed until saponification is completed (about 1 hour). Then, the organic solvent is largely evaporated in a vacuum and the product is precipitated at pH 1–2 by the addition of semiconcentrated aqueous hydrochloric acid. The title compound is suctioned off, washed with water and dried in a vacuum.

Yield: 2.33 g (99% of theory) of dark green crystals

Analysis (relative to anhydrous substance) C 61.96 H 5.20 Cl 2.54 Mn 3.94 N 8.03 O 18.34 Cld. C 61.88 H 5.45 Cl 2.76 Mn 3.79 N 7.82

EXAMPLE 12 a) Iron(III)-{5,10,15,20-tetrakis-{3-[(1-methylethyl)-oxycarbonyl-methoxy]-phenyl}-porphyrin}-acetate 3.97 g (3.68 mmol) of the compound produced under Example 2a and 8.0 g of iron(II) sulfate heptahydrate are refluxed in a mixture of 200 ml of acetic acid, 50 ml of pyridine and 10 ml of water for 2 hours. It is evaporated to dryness in a vacuum, the residue is taken up in 200 ml of dichloromethane and shaken out once with water and twice with saturated aqueous sodium bicarbonate solution. The organic phase is dried on anhydrous magnesium sulfate, filtered and concentrated by evaporation. The residue is recrystallized from water/isopropanol.

Yield: 3.95 g (90% of theory) of dark green crystals

Analysis (relative to anhydrous substance): C 66.50 H 5.33 Fe 4.68 Mn 3.94 N 4.70 O 18.79 Cld. C 66.44 H 5.51 Fe 4.61 Mn 3.79 N 4.53 b) Iron(III)-{5,10,15,20-tetrakis-[3-(carboxymethoxy)-phenyl]-porphyrin}-chloride 3.33 g (2.79 mmol) of the compound produced under Example 12a is dissolved in 150 ml of tetrahydrofuran. 150 ml of 2 n aqueous sodium hydroxide solution is added and refluxed until saponification is completed (about 1 hour). Then, the organic solvent is largely evaporated in a vacuum and the product is precipitated at pH 1–2 by the addition of semiconcentrated hydrochloric acid. The title compound is suctioned off, washed with water and dried in a vacuum.

Yield: 2.76 g (99% of theory) of dark green crystals

Analysis (relative to anhydrous substance) C 62.45 H 3.61 Cl 3.54 Fe 4.68 N 5.60 O 19.20 Cld. C 62.41 H 3.74 Cl 3.68 Fe 4.61 N 5.52

EXAMPLE 13 a) 5,10,15,20-Tetrakis-[3-(carboxymethoxy)-phenyl]-porphyrin, dihydrochloride 4.68 g (4.34 mmol) of the compound produced under Example 2a is dissolved in 100 ml of tetrahydrofuran. 100 ml of 2 n aqueous sodium hydroxide solution is added and refluxed until saponification is completed. Then, the organic solvent is largely evaporated in a vacuum, and the product is precipitated at pH 1–2 by the addition of semiconcentrated hydrochloric acid. The title compound is suctioned off, washed with water and dried in a vacuum.

Yield: 4.22 g (99% of theory) of dark green crystals

Analysis (relative to anhydrous substance) C 63.48 H 4.10 Cl 7.21 N 5.69 O 19.52 Cld. C 63.37 H 4.19 Cl 7.04 N 5.56 b) 5,10,15,20-Tetrakis-[3-(chlorocarbonylmethoxy)-phenyl]-porphyrin, dihydrochloride 3.07 g (3.12 mmol) of the compound produced according to Example 13a is refluxed for one hour in 150 ml of thionyl chloride after the addition of 0.05 ml of N,N-dimethylformamide. Then, it is evaporated to dryness in a vacuum and dried until the weight is constant.

Yield: 3.30 g (100% of theory) of green solid

Analysis (relative to anhydrous substance) C 59.06 H 3.43 Cl 20.11 N 5.30 O 12.10 Cld. C 59.17 H 3.50 Cl 20.39 N 5.14 c) 10,15,20-Tetrakis-[N,N',N'',N'''-(6-hydroxy-2,2-dimethyl-1,3-dioxepan-5-yl)-3-aminocarbonylmethoxyphenyl]-porphyrin 2.97 g (2.81 mmol) of the compound produced under Example 13b is dissolved in 150 ml of anhydrous dichloromethane. 1.70 g (16.8 mmol) of triethylamine and 2.72 g (16.8 mmol) of trans-6-amino-2,2-dimethyl-1,3-dioxepan-5-ol are added and stirred for 6 hours with exclusion of moisture at 20° C. Then, it is concentrated by evaporation and chromatographed on silica gel with dichloromethane/methanol, the product fractions are concentrated by evaporation and recrystallized from isopropanol/tert-butyl methyl ether.

Yield: 2.83 g (68% of theory) of violet crystals

Analysis (relative to anhydrous substance): C 64.77 H 6.11 N 7.55 O 21.57 Cld. C 64.57 H 6.30 N 7.63 O 21.57 d) Manganese(III)-{tetrakis-[N,N',N'',N'''-(6-hydroxy-2,2-dimethyl-1,3-dioxepan-5-yl)-3-aminocarbonylmethoxyphenyl]-porphyrin}-acetate 2.54 g (1.71 mmol) of the compound produced under Example 13c and 10 g of manganese(II) acetate tetrahydrate are stirred in a mixture of 200 ml of pyridine and 50 ml of water for about 3 hours at 80° C. It is concentrated by evaporation in a vacuum, the residue is taken up in 300 ml of dichloromethane of aqueous common salt solution, the organic phase is dried on anhydrous magnesium sulfate and filtered. The filtrate is concentrated by evaporation and the residue is recrystallized from aqueous ethanol.

Yield: 2.60 g (95% of theory) of dark green crystals

Analysis (relative to anhydrous substance) C 61.73 H 5.75 Mn 3.44 N 7.02 O 22.06 Cld. C 61.52 H 5.81 Mn 3.38 N 6.84 e) Manganese(III)-{tetrakis-[N,N',N'',N'''-[(1-RS,2-SR)-2,3-dihydroxy-1-hydroxymethylpropyl]-3-amino-carbonylmethoxyphenyl]-porphyrin}-chloride 2.11 g (1.32 mmol) of the compound produced under Example 13d is dissolved in 100 ml of methanol. 100 ml of 2 n hydrochloric acid is instilled and stirred for 3 hours at 20° C. After concentration by evaporation in a vacuum, the crude product is dissolved in methanol and precipitated by the addition of tert-butyl methyl ether.

Yield: 1.81 g (97% of theory) of dark green crystals

Analysis (relative to anhydrous substance) C 57.85 H 5.14 Cl 2.51 Mn 3.89 N 7.94 O 22.67 Cld. C 57.632 H 5.27 Cl 2.68 Mn 3.72 N 7.84

EXAMPLE 14

Production of a Contrast Medium for Nuclear-medicine Application: $^{64}$Cu or $^{67}$Cu Complex of 5,10,15,20-tetrakis-[3-(carboxymethoxy)-phenyl]-porphyrin 1.0 ml of a hydrochloric acid solution of 1.0 mCi $^{64}$CuCl$_2$ or $^{67}$CuCl$_2$ is adjusted to pH 7.5 with saturated aqueous sodium bicarbonate solution. 2.0 mg (2.2 mmol) of the compound produced under Example 13a) is added and the suspension is autoclaved for one hour at 120° C. After filtration with a membrane filter, a reddish filtrate which comprises virtually 100% of the activity used is obtained. The solution is ready for use.

EXAMPLE 15

Production of a Contrast Medium for Nuclear-medicine Application: $^{111}$In Complex of 5,10,15,20-tetrakis-[3-(carboxymethoxy)-phenyl]-porphyrin 1.0 ml of a hydrochloric acid solution of 1.0 mCi $^{111}$InCl$_3$ is adjusted to pH 7.5 with saturated, aqueous sodium bicarbonate solution. 2.0 mg (2.2 mmol) of the compound produced under Example 13a) is added and the suspension is autoclaved for one hour at 120° C. After filtration with a membrane filter, a reddish filtrate is obtained, which comprises virtually 100% of the activity used.

The solution is ready for use.

EXAMPLE 16

Production of a Contrast Medium for Nuclear-medicine Application: $^{99m}$Tc Complex of 5,10,15,20-tetrakis-[3-(carboxymethoxy)-phenyl]-porphyrin 2.2 mg (2.0 mmol) of the compound produced under Example 13a) is added to 1.0 ml of a solution of 1.8 mCi of $^{99m}$technetium(III) acetylacetate in DMSO and the solution is autoclaved for several hours at 130° C. Then, dissolved porphyrin is precipitated by the addition of 1.0 ml of tert-butyl methyl ether, suctioned off with a membrane filter, and it is taken up in 1.0 ml of pyrogen-free 0.1 molar aqueous sodium bicarbonate solution. After membrane filtration, the ready-to-use solution is obtained.

EXAMPLE 17

Determination of Compatibility and Relaxivity of the Compounds According to the Invention The compatibility was examined preliminarily in mice (NMRI, Schering SPF, female, about 25 g). 0.5 mmol/kg of the substance in each case was administered intravenously to a mouse. The animal died, the dose was halved and correspondingly moved, otherwise the corresponding dose was administered to 2 additional mice. The period of observation was 7 days. The compatibility is indicated with > if all animals tolerated the corresponding dose, with < if all died.

To determine the relaxivity, the relaxation times of the substances were measured in 4 different concentrations (0–1 mmol/l; dissolved in dist. water; pH 7.4) on a relaxometer (minispec pc120; 20 MHz; 40° C.). The calculation was performed from:

$$\Delta(1/T_{1,2}-1/T_{1,2}\text{blank value})/\Delta\text{conc.}=R_{1,2}(\text{linear regression}).$$

Results

Based on the better compatibility and the clearly higher relaxivity, the compounds according to the invention exhibit a clearly higher safety margin than that which corresponds to the prior art (e.g., EP 0 336 879 A 1).

| Compound after . . . | Compatibility mmol/kg | Relaxivity R1 l/mmol/s | Product Compatibility and Relaxivity |
|---|---|---|---|
| Example 2c | >0.5 | 13 | >6.5 |
| Example 4c | ≧0.5 | 11.6 | >5.8 |
| Example 2 from EP 0336 879 A1* | <0.5 | 8.6 | <4.3 |
| Example 4 from EP 0336 879 A1** | <0.25 | 8.8 | <2.2 |
| Example 17 from EP 0336 879 A1*** | <0.5 | 9.2 | <4.6 |

*Manganese (III)-{5,10,15,20-tetrakis-{[4-carboxylic acid-(2,3-dihydroxy-1-hydroxymethylpropyl)-amide]-phenyl}-porphyrin}-acetate
**Manganese (III)-[5,10,15,20-tetrakis-(3-carboxylatophenyl)-porphyrin]-acetate
***Manganese (III)-[5,10,15,20-tetrakis-(4-methoxy-3-sulfonatophenyl)-porphyrin]-acetate, tetrasodium salt

EXAMPLE 18

MR-Imaging Experiment of Tumor-bearing (Carcinoma of the Prostate) Nude Mice

Implementation

Imaging Parameters:

Bruker biospec (2.35 tesla; 100.33 MHz), nuclear spin tomography, Steglitz Hospital. Slice orientation, axial slice thickness: 4 mm, number of averages: 4/slice, field of view: 80 mm, matrix: $256^2$, 3–6 layers, 1 echo per imaging sequence, multislice variable echo (MSVE): $T_R$: 400, $T_E$: 25

Species:
Nude mouse, NMRI, nude/nude, male=25 g

Tumor Model:
Carcinoma of the prostate (MAT/Lu), implanted subcutaneously about 3 weeks before the beginning of the test, n=2–3 (per substance and dose).

Dosage:
0.05 and 0.1 mmol/kg of body weight i.v.

Formulation:
Compounds according to the invention were dissolved in tris-(hydroxymethyl)-aminomethane (50 mmol/l) NaCl—(100 mmol/l)—buffer (end concentration: 10 mmol/l; pH 7.5)

Results

The administration of 0.1 mmol/kg i.v. of the compounds according to the invention resulted (regardless of tumor size) in a good, relatively homogeneous enhancement in the tumor, which increased over the course of the tests (at least up to 120 minutes p.i.). In the liver and muscles, a somewhat comparable enhancement could be seen only immediately after administration, but it shrank continuously in contrast to that in the tumor, so that the tumor-tissue contrast constantly improved over the course of the imaging tests. Since the substance is eliminated mainly renally, the kidneys also appeared very bright even right after administration. However, the enhancement declined significantly faster in the kidneys than in the tumors, so that an improved tumor-tissue contrast (starting from about 60 minutes p.i.) was also observed here.

In the imaging tests with 0.05 mmol/kg i.v., comparable results were achieved overall (with a necessarily somewhat smaller signal rise).

EXAMPLE 19

MR-Imaging Experiment of Tumor-bearing (VX-2 Carcinoma) Rabbits

Implementation

Imaging Parameters:

Siemens magnetom® (1.5 tesla; 64 MHz), $T_1$-accentuated spin-echo technique: $T_R$: 350 ms, $T_E$: 15 ms. slice orientation: coronary, slice thickness: 3 mm, number of averages: 4 per layer, field of view: 150 mm, matrix: $256^2$, 4–6 layers, 1 echo per imaging sequence.

Species:
Hare rabbit, Wulf, female.=4 kg of body weight (KGW) [n=3].

Tumor Model:
Carcinoma (VX-2), implanted intramuscularly about 3 weeks before the beginning of the test.

Dosage:
0.05 and 0.1 mmol/kg of body weight i.v.

Results

The administration of reference substance Magnevist® at a dose of: 0.1 mmol/kg i.v. resulted only in a brief, small signal rise in the implanted tumor and in the lymph nodes examined on the tumor-bearing side and on the tumor-free side (iliacal and popliteal). Within about 60–90 minutes after administration, approximately the starting intensity was reached again in virtually all examined tissues and almost no enhancement of tumors or metastases was observed any longer.

The administration of 0.05 mmol/kg of body weight i.v., of the compounds according to the invention resulted in good prolonged enhancement both in the implanted tumor and in the majority of the lymph nodes on the tumor-bearing side. Judging from the pronounced enhancement in these lymph nodes or lymph node areas after administration of the compounds according to the invention, it was therefore possible to diagnose a metastasis involvement of the lymph nodes. The histological examination of the lymph nodes confirmed the results of the MR-tomographic examination.

| | Gd-DTPA: 0.1 mmol/kg of body weight i.v. | | | |
|---|---|---|---|---|
| minutes p.i. | lymph nodes (iliacal) | lymph node metastasis | VX-2 carcinoma | muscle |
| 0 | 1.00 | 1.00 | 1.00 | 1.00 |
| 2 | 1.50 | 1.61 | 1.50 | 1.20 |
| 8 | 1.32 | 1.44 | 1.50 | 1.11 |
| 17 | 1.20 | 1.36 | 1.48 | 1.10 |
| 42 | 1.24 | 1.29 | 1.47 | 1.07 |
| 52 | 1.17 | 1.20 | 1.42 | 1.02 |
| 69 | 1.11 | 1.25 | 1.40 | 1.08 |
| 24 hours p.i. | 1.14 | 0.97 | 1.11 | 1.04 |

Relative signal intensity in various tissues of a tumor-bearing (VX-2 carcinoma) rabbit (with metastasis in an iliacal lymph node) after one-time intravenous administration of Gd-DTPA (Magnevist®) (dose: 0.1 mmol/kg).

The output signal intensity ($=SI_{precontrast}$) in the various tissues was set at equal to 1 in each case.

| | Compound according to Example 2d): 0.05 mmol/kg of body weight i.v. (relative to Mcl of porphyrin) | | | |
|---|---|---|---|---|
| minutes p.i. | lymph nodes (iliacal) | lymph node metastasis | VX-2 carcinoma | muscle |
| 0 | 1.00 | 1.00 | 1.00 | 1.00 |
| 2 | 1.80 | 1.68 | 1.28 | 1.14 |
| 28 | 1.93 | 1.45 | 2.19 | 1.17 |
| 44 | 2.00 | 2.15 | 1.70 | 1.19 |
| 61 | 1.91 | 2.18 | 1.48 | 1.21 |
| 76 | 1.84 | 2.32 | 1.45 | 1.19 |
| 94 | 1.65 | 2.12 | 1.44 | 1.13 |
| 111 | 1.58 | 2.21 | 1.50 | 1.18 |
| 24 hours p.i. | 1.13 | 1.39 | 1.46 | 0.99 |

Relative signal intensity in various tissues of a tumor-bearing (VX-2 carcinoma) rabbit (with metastasis in an iliacal lymph node) after one-time intravenous administration of the compound according to the invention (dose: 0.05 mmol/kg) The output signal intensity ($=SI_{precontrast}$) in the various tissues was set at equal to 1 in each case.

We claim:
1. A porphyrin complex compound of:
a meso-tetraphenylporphyrin ligand of formula II

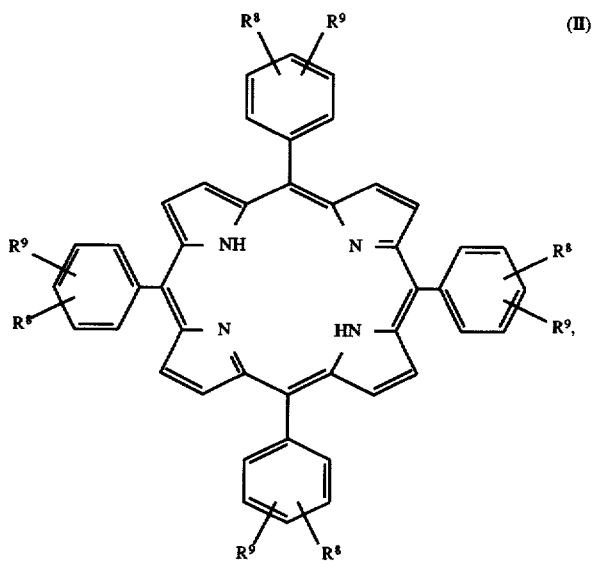

wherein $R^8$ is —$(O)_s$—$(CH_2)_k$—X—$CH_2$—Y—C(=O)—Z;

s is 0 or 1;

k is 0, 1, 2 or 3;

X is O, a direct bond or $NR^{10}$;

$R^{10}$ is $C_1-C_4$ acyl, $C_1-C_{10}$ alkylsulfonyl, benzenesulfonyl, $C_1-C_4$ alkylphenylene-sulfonyl, carboxy-$C_1-C_6$ alkyl or carboxy-$C_1-C_5$ acyl;

Y is a direct bond or —CHOH;

Z —OH or —$NR^{11}R^{12}$;

$R^{11}$ and $R^{12}$ are each, independently of one another, H or a straight-chain, branched-chain or cyclic, saturated or unsaturated hydrocarbon radical with up to 16 C atoms, optionally substituted by 1–6 hydroxy groups, with the proviso that there are no direct O—O or O—N bonds;

$R^9$ is H, F, Cl, Br, I, a straight-chain or branched $C_1-C_4$ alkyl, or —$(O)_s$—$(CH_2)_k$—X—$CH_2$—Y—C(=O)—Z; and an ion of an element of atomic numbers 21–32, 38, 39, 42–51 or 58–83; and wherein acid hydrogens present in $R^8$ and $R^9$ can optionally, in each case, be replaced by a physiologically harmless cation of an inorganic and/or organic base, amino acid or amino acid amide;

wherein said porphyrin complex compound is not a tin, iron, manganese or nickel complex of 5,10,15,20-tetrakis-[4-(carboxymethoxy)-phenyl]-porphyrin.

2. A porphyrin complex compound according to claim 1, wherein said compound is

Manganese(III)-{5,10,15,20-tetrakis-[3-(carboxymethoxy)-phenyl]-porphyrin}-chloride;

one of the 4 atropo-isomers of manganese(III)-{5,10,15,20-tetrakis-[2-(carboxymethyl)-phenyl]-porphyrin}-chloride;

Manganese(III)-{5,10,15,20-tetrakis-[3,4-bis-(carboxymethoxy)-phenyl]-porphyrin}-chloride;

Manganese(III)-{5,10,15,20-tetrakis-[(N-acetyl-N-carboxymethyl)-aminophenyl]-3-porphyrin}-chloride;

Manganese(III)-{5,10,15,20-tetrakis-[3-(carboxymethyl)-phenyl]-porphyrin}-chloride;

Manganese(III)-{5,10,15,20-tetrakis-[3-(2-carboxyethyl)-phenyl]-porphyrin}-chloride;

Manganese(III)-{5,10,15,20-tetrakis-{N,N-bis-(carboxymethyl)-3-aminophenyl-porphyrin}-chloride;

Manganese(III)-{5,10,15,20-tetrakis-[3-(2-carboxy-2-hydroxyethoxy)-phenyl]-porphyrin}-chloride;

Manganese(III)-{5,10,15,20-tetrakis-[N-carboxymethyl)-N-(p-toluenesulfonyl)-3-aminomethylphenyl]-porphyrin}-chloride;

Manganese(III)-{5,10,15,20-tetrakis-[{3-(N-acetyl-N-carboxylmethyl-3-aminopropyloxy)-phenyl]-porphyrin}-chloride;

Iron(III)-{5,10,15,20-tetrakis-[3-(carboxymethoxy)-phenyl]-porphyrin}-chloride;

Manganese(III)-{tetrakis-[N,N',N'',N'''-[(1-RS,2-SR)-2,3-dihydroxy-1-hydroxymethylpropyl]-3-aminocarbonylmethoxyphenyl]-porphyrin}-chloride;

Copper-64 or copper-67 complex of 5,10,15,20-tetrakis-[3-(carboxymethoxy)-phenyl]-porphyrin;

Indium(III) complex of 5,10,15,20-tetrakis-[3-(carboxymethoxy)-phenyl]-porphyrin; or Technetium-99m complex of 5,10,15,20-tetrakis-[3-(carboxymethoxy)-phenyl]-porphyrin.

3. A pharmaceutical composition comprising:
at least one complex compound according to claim 1, an aqueous medium, and optionally one or more conventional galenic additives.

4. A pharmaceutical composition according to claim 3, wherein said composition is sterilized.

5. In a method of NMR diagnosis, radiodiagnosis or radiotherapy comprising administering at least one porphyrin complex compound, the improvement wherein said compound is a compound according to claim 1.

6. A process for production of a porphyrin complex compound, said compound comprising a meso-tetraphenylporphyrin ligand of formula II

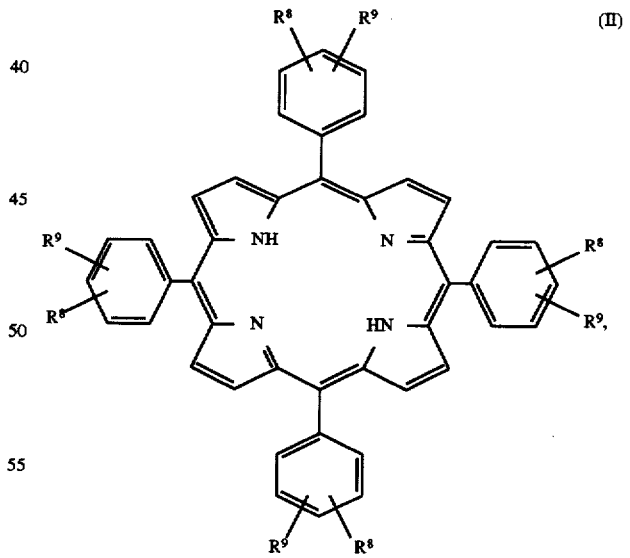

wherein $R^8$ is —$(O)_s$—$(CH_2)_k$—X—$CH_2$—Y—C(=O)—Z;

s is 0 or 1;

k is 0, 1, 2 or 3;

X is O, a direct bond or $NR^{10}$;

$R^{10}$ is $C_1-C_4$ acyl, $C_1-C_{10}$ alkylsulfonyl, benzenesulfonyl, $C_1-C_4$ alkylphenylene-sulfonyl, carboxy-$C_1-C_6$ alkyl or carboxy-$C_1-C_5$ acyl;

Y is a direct bond or —CHOH;

Z —OH or —NR$^{11}$R$^{12}$;

R$^{11}$ and R$^{12}$ are each, independently of one another, H or a straight-chain, branched-chain or cyclic, saturated or unsaturated hydrocarbon radical with up to 16 C atoms, optionally substituted by 1–6 hydroxy groups, with the proviso that there are no direct O—O or O—N bonds;

R$^9$ is H, F, Cl, Br, I, a straight-chain or branched C$_1$–C$_4$ alkyl, or —(O)$_s$—(CH$_2$)$_k$—X—CH$_2$—Y—C(=O)—Z; and an ion of an element of atomic numbers 21–32, 38, 39, 42–51 or 58–83; and optionally one or more physiologically harmless cation (s) of inorganic and/or organic bases, amino acids or amino acid amides;

wherein said complex compound is not a tin, iron, manganese or nickel complex of 5,10,15,20-tetrakis-[4-(carboxymethoxy)-phenyl]-porphyrin;

said process comprising saponifying a porphyrin of formula V

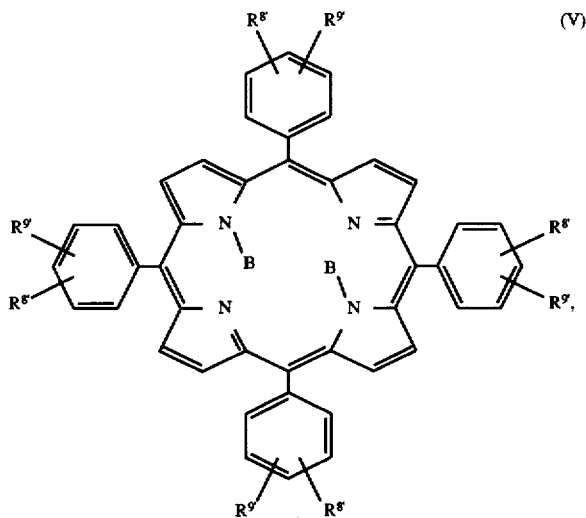

wherein

B is H or a metal ion equivalent of an element of atomic numbers 21–32, 38, 39, 42–51 or 58–83, R$^{8'}$ is —(O)$_s$—(CH$_2$)$_k$—X'—CH$_2$—Y'—C(=O)—Z';

X' and Y' have the meanings indicated for X and Y, respectively, except that functional groups, if present, are optionally protected;

Z' is a leaving group;

R$^{9'}$ is H, F, Cl, Br, I, a straight-chain or branched C$_1$–C$_4$ alkyl, or —(O)$_s$—(CH$_2$)$_k$—X—CH$_2$—Y—C(=O)—Z; or reacting said compound of formula V with an amine of formula VI

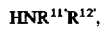 HNR$^{11'}$R$^{12'}$, (VI)

wherein

R$^{11'}$ and R$^{12'}$ have the meanings indicated for R$^{11}$ and R$^{12}$, respectively, except that hydroxy groups, if present, are optionally protected; cleaving protective groups, if present, and if B is H, reacting the resultant compound with a metal oxide or metal salt of an element of atomic numbers 21–32, 38, 39, 42–51 or 58–83;

wherein the sequence of the two last-mentioned reactions can be interchanged; and if acid hydrogen atom(s) are still present, optionally substituting cations of inorganic and/or organic bases, amino acids and amino acid amides, for said acid hydrogen atom(s).

7. A porphyrin complex compound according to claim 1, wherein said ion is of an element of atomic numbers 21–29, 42, 44 or 58–70.

8. A porphyrin complex compound according to claim 1, wherein said ion is a radioisotope of an element of atomic number 27, 29–32, 38, 39, 42–51, 62, 64, 70, 75, 77 or 81–83.

9. In a method of NMR imaging comprising administering a contrast agent, the improvement wherein said contrast agent is a porphyrin complex compound according to claim 7.

10. In a method of radiodiagnosis or radiotherapy comprising administering a contrast agent, the improvement wherein said contrast agent is a porphyrin complex compound according to claim 8.

11. A porphyrin complex compound according to claim 1, wherein said ion is manganese(III) ion.

12. A porphyrin complex compound according to claim 7, wherein said ion is chromium(III), manganese(III), iron(III), cobalt(II), cobalt(III), nickel(II), copper(II), praseodymium (III), neodymium(III), samarium(III), gadolinium(III), terbium(III), dysprosium(III), holmium(III), erbium(III) or ytterbium(III).

13. A porphyrin complex compound according to claim 8, wherein said ion is a radioisotope of copper, cobalt, gallium, germanium, yttrium, strontium, technetium, indium, ytterbium, gadolinium, samarium, thallium or iridium.

14. A porphyrin complex compound according to claim 1, wherein R$^{11}$ and R$^{12}$ are each independently of one another a saturated, unsaturated, straight-chain or branched-chain or cyclic hydrocarbon with 1–10 C atoms, optionally substituted by 1–5 hydroxy groups.

15. A compound according to claim 1, wherein the structure —(O)$_x$—(CH$_2$)$_k$—X—CH$_2$—Y—of group R$^8$ is —CH$_2$—, —CH$_2$—CH$_2$—, —O—CH$_2$—, N(CO—CH$_3$) CH$_2$—, N(CH$_3$)—CH$_2$—, —N(CH$_2$—COOH)CH$_2$—, —O—CH$_2$—(CHOH)—, —O—(CH$_2$)$_3$—N(CO—CH$_3$)— CH$_2$—, —CH$_2$—N(SO$_2$—C$_6$H$_4$—CH$_3$)—CH$_2$—, or —O—(CH$_2$)$_3$—N(SO$_2$—C$_6$H$_4$—CH$_3$)—CH$_2$—.

16. A compound according to claim 1, wherein said one or more physiologically harmless cations are selected from the ions of lithium, potassium, calcium, sodium, ethanolamine, diethanolamine, morpholine, glucamine, N,N-dimethylglucamine, N-methylglucamine, lysine, arginine and ornithine.

17. A composition according to claim 3, wherein said composition contains at least one galenical additive selected from physiologically harmless buffers, complexing agents, electrolytes and surfactants.

18. A method according to claim 9, wherein said contrast agent is administered, enterally or parenterally, in an amount of 0.01–0.50 mmol/kg of body weight.

19. A method according to claim 10, wherein said contrast agent is administered, enterally or parenterally, in an amount of 0.01 µmol–2.0 mmol/kg of body weight.

20. A porphyrin complex compound according to claim 1, wherein X in group R$^8$ is NR$^{10}$.

21. A porphyrin complex compound according to claim 20, wherein R$^{10}$ is formyl, acetyl, propionyl, n-butyryl, i-butyryl, methane-sulfonyl, ethane-sulfonyl, propane-sulfonyl, butane-sulfonyl, pentane-sulfonyl, hexane-sulfonyl, heptane-sulfonyl, octane-sulfonyl, nonane-sulfonyl, decane-sulfonyl, benzene-sulfonyl, p-toluene-sulfonyl, 4-ethyl-phenyl-sulfonyl, carboxyhexyl, carboxypentyl, carboxybutyl, carboxypropyl, carboxyethyl, carboxymethyl, 5-carboxyvaleroyl, 4-carboxybutyryl, 3-carboxypropionyl, carboxyacetyl or carboxycarbonyl.

22. A porphyrin complex compound according to claim 1, wherein Z in group $R^8$ is —$NR^{11}R^{12}$.

23. A porphyrin complex compound according to claim 22, wherein $R^{11}$ and $R^{12}$ are each, independently, methyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-hydroxy-2-methylbutyl, 3-hydroxy-2-methylbutyl, 4-hydroxy-2-methylbutyl, 2-hydroxyisobutyl, 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl or 2-methhoxyethyl.

24. A porphyrin complex compound according to claim 1, wherein Z in group $R^8$ is OH.

25. A porphyrin complex compound according to claim 1, wherein s in group is $R^8$ is 1.

26. A porphyrin complex compound comprising:
a meso-tetraphenylporphyrin ligand of formula II

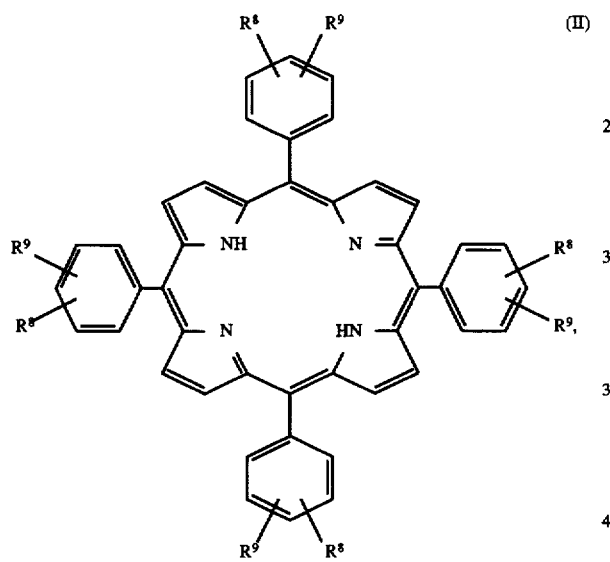

wherein $R^8$ is —$(O)_s$—$(CH_2)_k$—X—$CH_2$—Y—C(=O)—Z, with the proviso that $R^8$ is not 4-(carboxymethoxy)—;

s is 0 or 1;

k is 0, 1, 2 or 3;

X is O, a direct bond or $NR^{10}$;

$R^{10}$ is $C_1$–$C_4$ acyl, $C_1$–$C_{10}$ alkylsulfonyl, benzenesulfonyl, $C_1$–$C_4$ alkylphenylene-sulfonyl, carboxy-$C_1$–$C_6$ alkyl or carboxy-$C_1$–$C_5$ acyl;

Y is a direct bond or —CHOH;

Z —OH or —$NR^{11}R^{12}$;

$R^{11}$ and $R^{12}$ are each, independently of one another, H or a straight-chain, branched-chain or cyclic, saturated or unsaturated hydrocarbon radical with up to 16 C atoms, optionally substituted by 1–6 hydroxy groups, with the proviso that there are no direct O—O or O—N bonds;

$R^9$ is H, F, Cl, Br, I, a straight-chain or branched $C_1$–$C_4$ alkyl, or —$(O)_s$—$(CH_2)_k$—X—$CH_2$—Y—C(=O)—Z; and an ion of an element of atomic numbers 21–32, 38, 39, 42–51 or 58–83; and optionally one or more physiologically harmless cation (s) of inorganic and/or organic bases, amino acids or amino acid amides.

* * * * *